(12) United States Patent
Malik et al.

(10) Patent No.: US 10,618,030 B2
(45) Date of Patent: Apr. 14, 2020

(54) METAL OXIDE-BASED BIOCOMPATIBLE HYBRID SORBENT FOR THE EXTRACTION AND ENRICHMENT OF CATECHOLAMINE NEUROTRANSMITTERS AND RELATED COMPOUNDS, AND METHOD OF SYNTHESIS

(71) Applicant: UNIVERSITY OF SOUTH FLORIDA, Tampa, FL (US)

(72) Inventors: Abdul Malik, Tampa, FL (US); Abdullah Awadh Alhendal, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 302 days.

(21) Appl. No.: 15/639,449

(22) Filed: Jun. 30, 2017

(65) Prior Publication Data
US 2018/0001298 A1 Jan. 4, 2018

Related U.S. Application Data

(60) Provisional application No. 62/357,102, filed on Jun. 30, 2016.

(51) Int. Cl.
*G01N 1/40* (2006.01)
*G01N 30/08* (2006.01)
(Continued)

(52) U.S. Cl.
CPC .......... *B01J 20/226* (2013.01); *B01D 53/025* (2013.01); *B01J 20/041* (2013.01); *B01J 20/06* (2013.01); *B01J 20/08* (2013.01); *B01J 20/286* (2013.01); *B01J 20/28047* (2013.01); *B01J 20/28097* (2013.01); *B01J 20/291* (2013.01); *B01J 20/3085* (2013.01); *B01J 20/3204* (2013.01); *B01J 20/3208* (2013.01); *B01J 20/3221* (2013.01); *B01J 20/3231* (2013.01);
(Continued)

(58) Field of Classification Search
CPC .......... G01N 1/40; G01N 30/08; G01N 30/74; G01N 33/94
USPC ........................................... 436/111
See application file for complete search history.

(56) References Cited

U.S. PATENT DOCUMENTS 6,759,126 B1 * 7/2004 Malik ................ B01J 20/28014
428/375
6,783,680 B2 * 8/2004 Malik .................... B01J 20/103
210/198.2

(Continued)

OTHER PUBLICATIONS

Higuchi, T. et al, Journal of Materials Science 2000, 38, 3237-3243.*

(Continued)

*Primary Examiner* — Arlen Soderquist
(74) *Attorney, Agent, or Firm* — Saliwanchik, Lloyd & Eisenschenk

(57) ABSTRACT

The subject invention concerns metal or metalloid oxide-based sol-gel hybrid sorbent and methods of synthesis. In one embodiment, the sorbent is a $ZrO_2$ polypropylene oxide based sol-gel. The subject invention also concerns a hollow tube or capillary internally coated with a sorbent of the invention. Sorbent coated tubes and capillaries of the invention can be used in extraction and/or enrichment of samples to be analyzed for catecholamines and related compounds.

14 Claims, 8 Drawing Sheets

(51) Int. Cl.

| | | |
|---|---|---|
| *G01N 30/74* | (2006.01) | |
| *G01N 33/94* | (2006.01) | |
| *B01J 20/22* | (2006.01) | |
| *B01J 20/28* | (2006.01) | |
| *B01J 20/291* | (2006.01) | |
| *B01J 20/286* | (2006.01) | |
| *B01J 20/30* | (2006.01) | |
| *B01J 20/32* | (2006.01) | |
| *B01D 53/02* | (2006.01) | |
| *B01J 20/281* | (2006.01) | |
| *B01J 20/08* | (2006.01) | |
| *B01J 20/04* | (2006.01) | |
| *B01J 20/06* | (2006.01) | |

(52) U.S. Cl.
CPC ....... *B01J 20/3236* (2013.01); *B01J 20/3289* (2013.01); *G01N 1/405* (2013.01); *G01N 30/08* (2013.01); *G01N 30/48* (2013.01); *G01N 30/74* (2013.01); *G01N 33/9406* (2013.01); *G01N 33/9413* (2013.01); *B01J 2220/54* (2013.01); *B01J 2220/86* (2013.01)

(56) References Cited

U.S. PATENT DOCUMENTS

| | | | | |
|---|---|---|---|---|
| 6,998,040 B2* | 2/2006 | Malik | ............... | G01N 27/44704 204/600 |
| 7,407,568 B1* | 8/2008 | Malik | ................ | B01J 20/28047 204/455 |
| 7,622,191 B2* | 11/2009 | Malik | .................. | B01J 20/0211 428/432 |
| 7,629,424 B2* | 12/2009 | Malik | ........................ | C08J 3/28 526/240 |
| 7,947,174 B2* | 5/2011 | Malik | .................... | B01D 15/08 210/198.2 |
| 8,241,476 B1* | 8/2012 | Malik | ................ | B01J 20/28047 204/604 |
| 8,597,508 B2* | 12/2013 | Malik | .................... | B01D 15/08 210/198.2 |
| 8,603,833 B2* | 12/2013 | Malik | .................. | B01J 20/0251 204/455 |
| 8,623,279 B2* | 1/2014 | Malik | ...................... | B01J 20/26 210/198.2 |
| 8,685,240 B2* | 4/2014 | Malik | .................. | B01D 15/206 210/198.2 |
| 9,528,921 B2* | 12/2016 | Malik | .................... | G01N 1/405 |
| 9,555,394 B2* | 1/2017 | Malik | ..................... | B01J 20/26 |
| 2002/0150923 A1* | 10/2002 | Malik | .................. | B01J 20/103 435/6.1 |
| 2003/0075447 A1* | 4/2003 | Malik | ............... | G01N 27/44704 204/454 |
| 2003/0213732 A1* | 11/2003 | Malik | .................... | B01D 15/08 210/94 |
| 2004/0129141 A1* | 7/2004 | Malik | .................... | B01D 15/206 96/101 |
| 2005/0106068 A1* | 5/2005 | Malik | ................ | B01J 20/28047 422/89 |
| 2006/0013981 A1* | 1/2006 | Malik | .................... | B01J 20/285 428/36.91 |
| 2006/0013982 A1* | 1/2006 | Malik | .................. | B01J 20/0211 428/36.91 |
| 2006/0113231 A1* | 6/2006 | Malik | .................... | B01J 20/103 210/198.2 |
| 2007/0062874 A1* | 3/2007 | Malik | .................. | B01D 15/206 210/656 |
| 2007/0095736 A1* | 5/2007 | Malik | ................ | B01J 20/28047 210/198.2 |
| 2007/0172960 A1* | 7/2007 | Malik | .................... | G01N 30/56 436/161 |
| 2009/0250349 A1* | 10/2009 | Malik | ................ | B01J 20/28047 204/605 |
| 2010/0112208 A1* | 5/2010 | Malik | .................. | B01J 20/0211 427/235 |
| 2012/0000850 A1* | 1/2012 | Malik | .................... | B01D 15/08 210/635 |
| 2012/0004434 A1* | 1/2012 | Malik | .................... | B01D 15/38 556/10 |
| 2012/0024790 A1* | 2/2012 | Malik | .................. | B01J 20/0251 210/656 |
| 2012/0128551 A1* | 5/2012 | Abdul | ...................... | B01J 20/26 422/527 |
| 2013/0071945 A1* | 3/2013 | Malik | .................... | G01N 1/405 436/178 |
| 2014/0057048 A1* | 2/2014 | Malik | ...................... | B01J 20/26 427/235 |

OTHER PUBLICATIONS

Bigham, S. et al, Analytical Chemistry 2002, 74, 752-761.*
Kim, T.-Y. et al, Journal of Chromatography A 2004, 1047, 165-174.*
Alhooshani, K. et al, Journal of Chromatography A 2005, 1062, 1-14.*
Bagheri, H. et al, Journal of Chromatography B 2005, 818, 147-157.*
Liu, M. et al, Journal of Chromatography A 2006, 1108, 149-157.*
Farhadi, K. et al, Talanta 2009, 77, 1285-1289.*
Maleki, R. et al, Chromatographia 2009, 69, 775-778.*
Walcarius, A. et al, Annual Review of Analytical Chemistry 2009, 2, 121-141.*
Segro, S. S. et al, Journal of Chromatography A 2009, 1216, 4329-4338.*
Shearrow, A. M. et al, Journal of Chromatography A 2009, 1216, 6349-6355.*
Farhadi, K. et al, Journal of Separation Science 2010, 33, 88-92.*
Segro, S. S. et al, Analytical Chemistry 2010, 82, 4107-4113.*
Segro, S. S. et al, Journal of Separation Science 2010, 33, 3075-3096.*
Kabir, A. et al, Trends in Analytical Chemistry 2013, 45, 197-218.*
Celikbicak, O. et al, Analyst 2013, 138, 4403-4410.*
Alhendal, A. et al, Journal of Chromatography A 2016, 1468, 23-32.*
Tsubokawa, N. et al, Colloid & Polymer Science 1989, 267, 511-515.*
Dahmouche, K. et al, Journal of Physical Chemistry B 1999, 103, 4937-4942.*
Shende, C. et al, Analytical Chemistry 2003, 75, 3518-3530.*
Mariotti, M. P. et al, Journal of the Brazilian Chemical Society 2006, 17, 689-696.*
Ankireddy, S. R. et al. "Selective detection of dopamine in the presence of ascorbic acid via fluorescence quenching of InP/ZnS quantum dots" *International Journal of Nanomedicine*, Aug. 25, 2015, pp. 113-119, vol. 10.
Aronne, A. et al. "Use of a New Hybrid Sol-Gel Zirconia Matrix in the Removal of the Herbicide MCPA: A Sorption/Degradation Process" *Environmental Science & Technology*, Dec. 19, 2011, pp. 1755-1763, vol. 46.
Bagheri, H. et al. "Towards greater mechanical, thermal and chemical stability in solid-phase microextraction" *Trends in Analytical Chemistry*, 2012, pp. 126-139, vol. 34.
Baranyi, M. et al. "Chromatographic analysis of dopamine metabolism in a Parkinsonian model" *Journal of Chromatography A*, 2006, pp. 13-20, vol. 1120.
Bilecka, I. et al. "New developments in the nonaqueous and/or non-hydrolytic sol-gel synthesis of inorganic nanoparticles" *Electrochimica Acta*, 2010, pp. 7717-7725, vol. 55.
Bu, Y. et al. "Facile and efficient poly(ethylene terephthalate) fibers-in-tube for online solid-phase microextraction towards polycyclic aromatic hydrocarbons" *Anal. Bioanal. Chem.* 2016, pp. 4871-4882, vol. 408, No. 18.
Chang, C-C. et al. "Preparation and characterization of polymer/zirconia nanocomposite antistatic coatings on plastic substrates" *Journal of Coatings Technology and Research*, 2013, pp. 73-78, vol. 10, No. 1.

(56) References Cited

OTHER PUBLICATIONS

Chen, Z. et al. "On-Line Monolithic Enzyme Reactor Fabricated by Sol-Gel Process for Elimination of Ascorbic Acid While Monitoring Dopamine" *Electroanalysis*, 2005, pp. 231-238, vol. 17, No. 3.

Chen, L-Q. et al. "Selective extraction of catecholamines by packed fiber solid-phase using composite nanofibers composing of polymeric crown ether with polystyrene" *Biomedical Chromatography*, 2015, pp. 103-109, vol. 29.

Chitravathi, S. et al. "Simultaneous Determination of Catecholamines in Presence of Uric Acid and Ascorbic Acid at a Highly Sensitive Electrochemically Activated Carbon Paste Electrode" *Journal of the Electrochemical Society*, 2015, pp. B163-B172, vol. 162, No. 7.

Chong, S. L. et al. "Sol-Gel Coating Technology for the Preparation of Solid-Phase Microextraction Fibers of Enhanced Thermal Stability" *Analytical Chemistry*, Oct. 1, 1997, pp. 3889-3898, vol. 69, No. 19.

Claude, B. et al. "Selective Solid-Phase Extraction of Catecholamines and Metanephrines from Serum Using a New Molecularly Imprinted Polymer" *Journal of Liquid Chromatography & Related Technologies*, 2014, pp. 2624-2638, vol. 37.

Debecker, D. P. et al. "Non-hydrolytic sol-gel routes to heterogeneous catalysts" *Chemical Society Reviews*, 2012, pp. 3624-3650, vol. 41.

Debecker, D. P. et al. "Mesoporous mixed oxide catalysts via non-hydrolytic sol-gel: A review" *Applied Catalysis A*, 2013, pp. 192-206, vol. 451.

De Bellaistre, M. C. et al. "Control of electroosmotic flow in zirconia-coated capillaries" *Journal of Chromatography A*, 2002, pp. 199-205, vol. 971.

Dunand, M. et al. "High-Throughput and Sensitive Quantitation of Plasma Catecholamines by Ultraperformance Liquid Chromatography-Tandem Mass Spectrometry Using a solid Phase Microwell Extraction Plate" *Analytical Chemistry*, Feb. 22, 2013, pp. 3539-3544, vol. 85.

Fang, L. et al. "Germania-Based, Sol-Gel Hybrid Organic-Inorganic Coatings for Capillary Microextraction and Gas Chromatography" *Analytical Chemistry*, Dec. 15, 2007, pp. 9441-9451, vol. 79, No. 24.

Fang, Z. et al. "Hydrolysis of $ZrCl_4$ and $HfCl_4$: The Initial Steps in the High-Temperature Oxidation of Metal Chlorides to Produce $ZrO_2$ and $HfO_2$" *The Journal of Physical Chemistry*, Mar. 8, 2013, pp. 7459-7474, vol. 117.

Ferrer, D. G. et al. "Analysis of epinephrine, norepinephrine, and dopamine in urine samples of hospital patients by micellar liquid chromatography" *Analytical and Bioanalytical Chemistry*, Oct. 1, 2015, pp. 9009-9018, vol. 407.

Ferry, B. et al. "Analysis of microdialysate monoamines, including noradrenaline, dopamine and serotonin, using capillary ultra-high performance liquid chromatography and electrochemical detection" *Journal of Chromatography B*, 2014, pp. 52-57, vols. 951-952.

Fujita, K. "Development of Non-Siliceous Porous Materials and Emerging Applications" *Bulletin of the Chemical Society of Japan*, Apr. 10, 2012, pp. 415-432, vol. 85, No. 4.

Fumes, B. H. et al. "Recent advances and future trends in new materials for sample preparation" *Trends in Analytical Chemistry*, 2015, pp. 9-25, vol. 71.

Gawel, B. et al. "Sol-Gel Synthesis of Non-Silica Monolithic Materials" *Materials*, 2010, pp. 2815-2833, vol. 3.

Hayes, J. D. et al, "Sol-gel chemistry-based Ucon-coated columns for capillary electrophoresis" *Journal of Chromatography B*, 1997, pp. 3-13, vol. 695.

Hayes, J. D. et al. "Sol-gel Monolithic Columns with Reversed Electroosmotic Flow for Capillary Electrochromatography" *Analytical Chemistry*, Sep. 1, 2000, pp. 4090-4099, vol. 72, No. 17.

Jeevajothi, K. et al. "Transparent, non-fluorinated, hydrophobic silica coatings with improved mechanical properties" *Ceramics International*, 2013, pp. 2111-2116, vol. 39.

Ji, C. et al. "Diethylation Labeling Combined with UPLC/MS/MS for Simultaneous Determination of a Panel of Monoamine Neurotransmitters in Rat Prefrontal Cortex Microdialysates" *Analytical Chemistry*, Dec. 1, 2008, pp. 9195-9203, vol. 80, No. 23.

Kartsova, L. A. et al. "Determination of Catecholamines by Capillary Electrophoresis and Reversed-Phase High-Performance Liquid Chromatography" *Journal of Analytical Chemistry*, 2004, pp. 737-741, vol. 59, No. 8.

Kelly, J. A. et al. "Sol-gel precursors for group 14 nanocrystals" *Chemical Communications*, 2010, pp. 8704-8718, vol. 46.

Lasáková, M. et al. "Molecularly imprinted polymer for solid-phase extraction of ephedrine and analogs from human plasma" *Journal of Separation Science*, 2009, pp. 1036-1042, vol. 32.

Li, X. et al. "A scratch-resistant and hydrophobic broadband antireflective coating by sol-gel method" *Thin Solid Films*, 2011, pp. 6236-6240, vol. 519.

Lin, T-H. et al. "Selective enrichment of catecholamines using iron oxide nanoparticles followed by CE with UV detection" *Electrophoresis*, 2013, pp. 297-303, vol. 34.

Livage, J. et al. "Sol-gel chemistry of transition metal oxides" *Progress in Solid State Chemistry*, 1988, pp. 259-341, vol. 18.

Ma, H-F. et al. "Electrochemical determination of dopamine using octahedral $SnO_2$ nanocrystals bound to reduced graphene oxide nanosheets" *Microchim Acta*, 2015, pp. 2001-2007, vol. 182.

Malik, A. et al. "New Directions in the Design and Synthesis of Sol-Gel Media for the Extraction and/or Preconcentration of Biologically and Environmentally Important Molecules" abstract presented at 18th International Symposium on Advances in Extraction Technologies (ExTech 2016), Torun, Poland, Jul. 3-6, 2016.

Manger, W. M. et al. "How to Diagnose, How to Treat—Pheochromocytoma" *The Journal of Clinical Hypertension*, Jan./Feb. 2002, pp. 62-72, vol. 4, No. 1.

McCalley, D. V. "Evaluation of reversed-phase columns for the analysis of very basic compounds by high-performance liquid chromatography: Application to the determination of the tobacco alkaloids" *Journal of Chromatography*, 1993, pp. 213-220, vol. 636.

Minami, T. "Advanced sol-gel coatings for practical applications" *Journal of Sol-Gel Science and Technology*, 2013, pp. 4-11, vol. 65.

Morselli, D. et al. "Double role of polyethylene glycol in the microwaves-assisted non-hydrolytic synthesis of nanometric $TiO2$: Oxygen source and stabilizing agent" *Journal of Nanoparticle Research*, Sep. 16, 2014, pp. 2645-1-2645-11, vol. 16.

Mutin, P. H. et al. "Nonhydrolytic Processing of Oxide-Based Materials: Simple Routes to Control Homogeneity, Morphology, and Nanostructure" *Chemistry of Materials*, 2009, pp. 582-596, vol. 21, No. 4.

Nagarajan, S. et al. "Nanocomposite Coatings on Biomedical Grade Stainless Steel for Improved Corrosion Resistance and Biocompatibility" *ACS Applied Materials & Interfaces*, Sep. 11, 2012, pp. 5134-5141, vol. 4.

Nawrocki, J. et al. "Part I. Chromatography using ultra-stable metal oxide-based stationary phases for HPLC" *Journal of Chromatography A*, 2004, pp. 1-30, vol. 1028.

Oasis Sample Extraction Products Brochure. Waters Literature Notes. Publication No. 720001692EN. Retrieved from the internet on Aug. 10, 2018, www.waters.com/waters/library.htm?cid=511436&lid=1529729&locale=en_US.

Pacak, K. et al. "Pheochromocytoma: recommendations for clinical practice from the First International Symposium" *Nature Clinical Practice*, Feb. 2007, pp. 92-102, vol. 3, No. 2.

Pastoris, A. et al. "Automated analysis of urinary catecholamines by high-performance liquid chromatography and on-line sample pretreatment" *Journal of Chromatography B*, 1995, pp. 287-293, vol. 664.

Phenylboronic Acid (PBA) Solid Phase Extraction Mechanisms and Applications. Agilent Technologies Technical Overview. Publication No. SI-02442. 2010.

Piest, M. et al. "pH-responsive, dynamically restructuring hydrogels formed by reversible crosslinking of PVA with phenylboronic acid functionalised PPO-PEO-PPO spacers (Jeffamines®)" *Soft Matter*, 2011, pp. 11111-11118, vol. 7.

Pinna, N. et al. "Surfactant-Free Nonaqueous Synthesis of Metal Oxide Nanostructures" *Angewandte Chemie International Edition*, 2008, pp. 5292-5304, vol. 47.

(56) References Cited

OTHER PUBLICATIONS

Randon, J. et al. "Synthesis of zirconia monoliths for chromatographic separations" *Journal of Chromatography A*, 2006, pp. 19-25, vol. 1109.

Rozet, E. et al. "Performances of a multidimensional on-line SPE-LC-ECD method for the determination of three major catecholamines in native human urine: Validation, risk and uncertainty assessments" *Journal of Chromatogrvhy B*, 2006, pp. 251-260, vol. 844.

Sabbioni, C. et al. "Simultaneous liquid chromatographic analysis of catecholamines and 4-hydroxy-3-methoxyphenylethylene glycol in human plasma: Comparison of amperometric and coulometric detection" *Journal of Chromatography A*, 2004, pp. 65-71, vol. 1032.

Saracino, M. A. et al. "Microextraction by packed sorbent (MEPS) to analyze catecholamines in innovative biological samples," *J. Pharm. Biomed. Anal.*, 2015, pp. 122-129, vol. 104.

Segro, S. S. et al. "High-temperature solvent stability of sol-gel Germania triblock polymer coatings in capillary microextraction on-line coupled to high-performance liquid chromatography" *Journal of Chromatography A*, 2010, pp. 5746-5752, vol. 1217.

Skinner, H. A. et al. "Metal-ligand bond-energies in organometallic compounds" *Pure & Applied Chemistry*, 1985, pp. 79-88, vol. 57, No. 1.

Strenger, V. et al. "Diagnostic and Prognostic Impact of Urinary Catecholamines in Neuroblastoma Patients" *Pediatric Blood Cancer*, 2007, pp. 504-509, vol. 48.

Sudha, M. et al. "Synthesis, characterization and study of photocatalytic activity of surface modified ZnO nanoparticles by PEG capping" *Journal of Sol-Gel Science and Technology*, 2013, pp. 301-310, vol. 65.

Suh, D. J. et al. "Synthesis of High-Surface-Area Zirconia Aerogels with a Well-Developed Mesoporous Texture Using $CO_2$ Supercritical Drying" *Chemistry of Materials*, 2002, pp. 1452-1454, vol. 14, No. 4.

Talwar, D. et al. "Extraction and separation of urinary catecholamines as their diphenyl boronate complexes using C18 solid-phase extraction sorbent and high-performance liquid chromatography" *Journal of Chromatography B*, 2002, pp. 341-349, vol. 769.

Thomas, A. et al. "Quantitative Determination of Adrenaline and Noradrenaline in Urine Using Liquid Chromatography-Tandem Mass Spectrometry" *Chromatographia*, Nov. 2006, pp. 587-591, vol. 64, No. 9/10.

Tran, M. et al. "Tantala-Based Sol-Gel coating for capillary microextraction on-line coupled to high performance liquid chromatography" *J. Chromatogr. A*, 2017, pp. 38-47, vol. 1522.

Unger, K. K. et al. "Adsorbents and columns in analytical high-performance liquid chromatography: A perspective with regard to development and understanding" *Journal of Separation Science*, 2012, pp. 1201-1212, vol. 35.

Vlčková, M. et al. "Determination of cationic neurotransmitters and metabolites in brain homogenates by microchip electrophoresis and carbon nanotube-modified amperometry" *Journal of Chromatography A*, 2007, pp. 214-221, vol. 1142.

Vuorensola, K. et al. "Determination of urinary catecholamines with capillary electrophoresis after solid-phase extraction" *Journal of Chromatography A*, 2000, pp. 317-327, vol. 895.

Wang, D. et al. "Sol-Gel Column Technology for Single-Step Deactivation, Coating, and Stationary-Phase Immobilization in High-Resolution Capillary Gas Chromatography" *Analytical Chemistry*, 1997, pp. 4566-4576, vol. 69.

Wang, S-C. et al. "Determination of highly polar catecholamine with liquid chromatography-tandem mass spectrometry using weak cation-exchange stationary phase to increase retention time" *Microchemical Journal*, 2007, pp. 163-169, vol. 87.

Whiting, M. J. "Simultaneous measurement of urinary metanephrines and catecholamines by liquid chromatography with tandem mass spectrometric detection" *Annals of Clinical Biochemistry*, 2009, pp. 129-136, vol. 46.

Yoldas, B. E. "Hydrolysis of titanium alkoxide and effects of hydrolytic polycondensation parameters" *Journal of Materials Science*, 1986, pp. 1087-1092, vol. 21.

Zhang, X. et al. "Molecularly imprinted solid phase microextraction fiber for trace analysis of catecholamines in urine and serum samples by capillary electrophoresis" *Talanta*, 2012, pp. 270-276, vol. 99.

\* cited by examiner

- Biomarkers (neurotransmitters)

Dopamine

Epinephrine

Serotonin

- Catecholamines metabolites

4-hydroxy-3-methoxyphenyl glycol (HMPG)

Homovanillic acid (HMV)

Vanillylmandelic acid (VMA)

- Analytical probes related to biomarkers and their metabolites

Acetaminophen

Vanillin

Benzoic acid 4-hydroxybenzoic acid

Quinol

Catechol

Resorcinol

METAL OXIDE-BASED BIOCOMPATIBLE HYBRID SORBENT FOR THE EXTRACTION AND ENRICHMENT OF CATECHOLAMINE NEUROTRANSMITTERS AND RELATED COMPOUNDS, AND METHOD OF SYNTHESIS

CROSS-REFERENCE TO RELATED APPLICATION

The present application claims the benefit of U.S. Provisional Application Ser. No. 62/357,102, filed Jun. 30, 2016, which is hereby incorporated by reference herein in its entirety, including any figures, tables, nucleic acid sequences, amino acid sequences, or drawings.

BACKGROUND OF THE INVENTION

Analytical tools for efficient extraction, preconcentration and detection of catecholamines (dopamine, epinephrine and norepinephrine) in biological matrices (such as urine) are important from a clinical point of view. Catecholamines have been investigated as potential biomarkers for the diagnosis and monitoring of tumors associated with different types of cancers and neural disorders [1]. Excess production of catecholamines by these tumors can cause "hypercatecholaminemia" which may cause health complications such as cerebrovascular accident, heart failure, cardiomyopathy and other potent impacts on the cardiovascular system [2]. Catecholamines are excreted in urine mainly in the following forms: deaminated metabolites, unchanged, and o-methylated amines (metanephrines). Analyzing catecholamines in urine, plasma or blood samples require sample preparation, preconcentration and cleanup steps essential for the minimization of any interfering components that might be present in biological matrices. In current practices, catecholamine sample pretreatments are predominantly performed by solid phase extraction (SPE) utilizing two types of sorbents: (a) polymeric reversed-phase resins (e.g., Oasis HLB from WATERS, and PLRP-SPE from Agilent) and (b) phenylboronic acid-functionalized silica particles. Polymeric sorbents are typically made of N-methylpyrrolidone and divinylbenzene monomers [3], and they possess excellent pH stabilities as well as balanced hydrophilic-hydrophobic characteristics. However, the low specific affinity toward the polar catecholamines can be enhanced through their chemical modification (derivatization). This is typically accomplished via formation of diphenylboronate-catecholamine complex [4] to facilitate their analysis by HPLC [5] or capillary electrophoresis [6]. A notable shortcoming is that extraction beds prepared from organic polymers possesses slow mass transfer characteristics analogous to the chromatographic stationary phases prepared from polymeric materials [7]. This may result in delayed or incomplete desorption of the extracted analytes from the sorbent bed causing sample loss and/or carryover problems.

The other type of extraction media used for the analysis of catecholamines is based-on silica particles with phenylboronic acid ligand (PBA-SPE). They have been widely used and commercialized by Agilent. Phenylboronic acid ligand has high affinity toward cis-diol groups present in the catecholamines [8]. The activation of the complexation ligand (phenylboronate, pKa ~9.5 [9]) requires conditioning of the SPE cartridge with high-pH buffer (pH 10-12) [10] giving rise to the main drawback of PBA-SPE cartridges due to inadequate pH stability of silica-based particles known to have narrow operational pH window (pH 2-8) [11-14].

Malik and coworkers [15-18] have developed a number of sol-gel extraction phases for capillary microextraction (CME) coupled to gas chromatography (GC) or high-performance liquid chromatography (HPLC) providing excellent pH stability (0.0~14.0) using different metal/metalloid alkoxide precursors providing titania-[19,20], zirconia-[16], and germania-based [14,17,18] hybrid organic-inorganic coatings for capillary microextraction. Hydrolytic sol-gel (HSG) route [11] was used to create those microextraction media. Non-hydrolytic sol-gel (NHSG) route has been investigated extensively in the field of catalysis for the creation of metal/metalloid oxides [21,22]. In water-free environment, transition metal halide (e.g., $ZrCl_4$) concurrently undergoes alcoholysis and condensation reactions leading to the formation of transition metal oxides [23]. NHSG transition metal oxides possess (a) high homogeneity, (b) more Lewis acid sites than Bronsted acid-base sites and (c) better water-tolerance [21,22,24-26]. NHSG route can provide uniformly dispersed transition metal oxide particles in organic solvents and allows surface modification with organic moieties [27-30]. The latter property is a crucial point for the use of NHSG route for the creation of hybrid organic-inorganic material with covalent bonding between the organic ligand and the transition metal oxide network. Described herein is the synthesis and analytical evaluation of a novel zirconia-based sol-gel hybrid organic-inorganic sorbent to provide a biocompatible extraction medium integrating amphiphilic properties with enhanced thermal-, mechanical- and pH stability characteristics for the analysis of aqueous samples containing free catecholamines and molecules structurally related to their metabolites (FIG. 1).

BRIEF SUMMARY OF THE INVENTION

The subject invention concerns metal or metalloid oxide-based sol-gel hybrid sorbent and methods of synthesis. In one embodiment, the sorbent is a $ZrO_2$ polypropylene oxide based sol-gel. The subject invention also concerns a hollow tube or capillary internally coated with a sorbent of the invention. Sorbent coated tubes and capillaries of the invention can be used in extraction and/or enrichment of samples to be analyzed for catecholamines and related compounds (such as molecules structurally related to catecholamine metabolites).

DETAILED DESCRIPTION OF THE INVENTION

Figure 1:
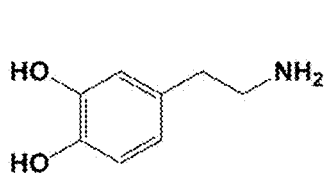
FIG. 1. Illustration of the chemical structure of catecholamines, their metabolites and chemical analogs related to the biomarkers and their metabolites.
Figure 1:
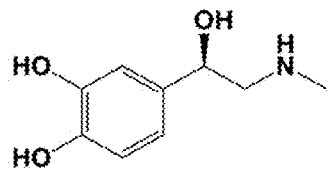
Figure 1:
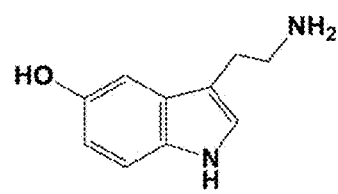
Figure 1:
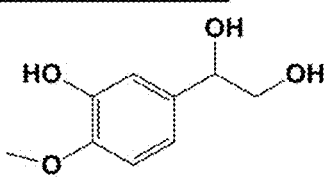
Figure 1:
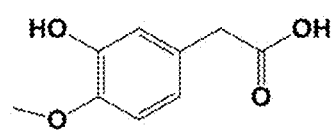
Figure 1:
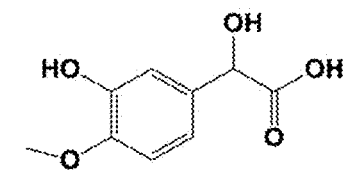
Figure 1:
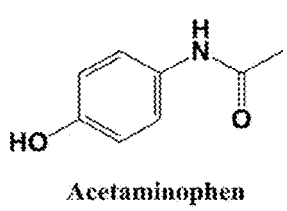
Figure 1:
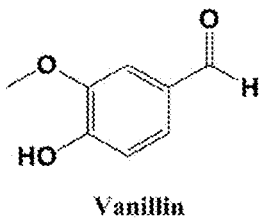
Figure 1:
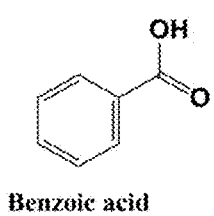
Figure 1:
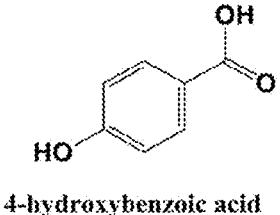
Figure 1:
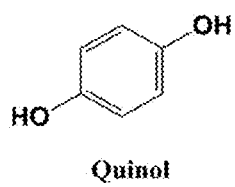
Figure 1:
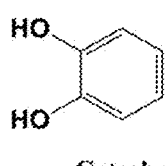
Figure 1:
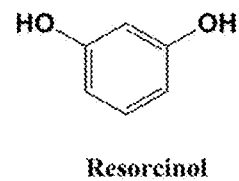

The subject invention concerns metal and metalloid oxide-based sol-gel hybrid sorbents and methods for synthesizing them. Metals and metalloids contemplated within the scope of the invention include, but are not limited to aluminum, antimony, arsenic, barium, beryllium, bismuth, boron, cadmium, cerium, chromium, cobalt, copper, dysprosium, erbium, europium, gadolinium, gallium, gold, hafnium, holmium, indium, iridium, iron, lanthanum, lithium, magnesium, manganese, molybdenum, neodymium, nickel, niobium, osmium, palladium, platinum, praseodymium, rhodium, ruthenium, samarium, scandium, selenium, silver, strontium, tellurium, terbium, thallium, thulium titanium, tantalum, vanadium, yttrium, zirconium, zinc, tungsten, or any combination thereof. The polymer utilized in the sol-gel can be any bio-compatible polymer or bio-compatible ligand having a sol-gel active end group or end groups. Examples of biocompatible polymers include, but are not limited to, poly(propylene oxide), poly(ethylene glycol), poly(vinyl alcohol), poly(lactic acid), poly(glycolic acid), poly(lactic-co-glycolic acid), poly(glutamic acid), poly(vinylpyrrolidone), poly(acrylamide), poly(N-isopropyl acrylamide), poly(acrylate), poly(methacrylate), poly(methyl methacrylate), poly(hydroxyethyl methacrylate), poly(N-(2-hydroxyethyl)methacrylate), poly(phosphoester)s, poly(phosphazene)s, poly(siloxane)s, chitosan, dextran, cellulose, hydroxyethyl cellulose, hydroxypropyl cellulose, hydroxypropyl methyl cellulose, poly(tetrahydrofuran), and their derivatives, and various combinations of the polymers and their derivatives providing co-polymers and block polymers. In a specific embodiment, the polymer is poly(propylene oxide). Examples of biocompatible ligands include, but are not limited to alkylene glycols (such as ethylene glycol, propylene glycol, butylene glycol, etc.), inositol, cyclodextrins, calixarenes, crown ethers, resorcinarenes, and their derivatives, and various combinations of the ligand and their derivatives. Sol-gel active end groups of the polymer or ligand contemplated include, but are not limited to, hydroxyl group, alkoxy group, derivatized hydroxyl group, derivatized alkoxy groups, and any combination thereof. The polymer or ligand can be chemically anchored in the sol-gel network via chemical bonding of one end of the polymer or ligand (the other end being free), chemical bonding of both/all ends of the polymer or ligand, or any combination thereof. In one embodiment, the sol-gel sorbent is a $ZrO_2$ polypropylene oxide ($ZrO_2$PPO) based sol-gel. In a specific embodiment, the $ZrO_2$PPO comprises the structure:

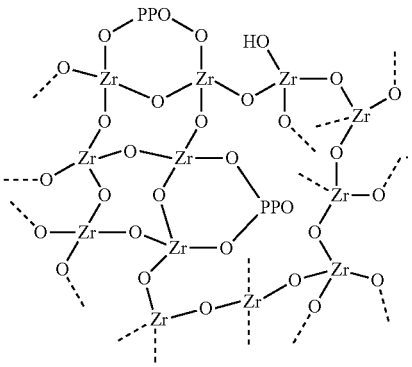

The PPO can have the structure:

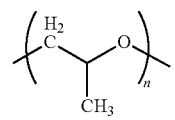

wherein n is an integer ≥1.

The subject invention also concerns a hollow tube or capillary coated with a sorbent composition of the invention on the interior of the tube or capillary. A coated tube or capillary of the invention can be used as a CME coupled to GC or HPLC analytical devices. The tube or capillary can be composed of or have an inner surface of any suitable material including, but not limited to, glass, fused silica, alumina, titania, zirconia, or polymeric hollow fibers. In one embodiment, the tube or capillary is made of fused silica. In a specific embodiment, the fused silica capillary is hydrothermally treated fused silica. In one embodiment, a sorbent of the invention is attached to Si of fused silica capillary or tube. In a specific embodiment, a sorbent of the invention is attached to the inner surface of a fused silica capillary or tube and comprises the structure shown below:

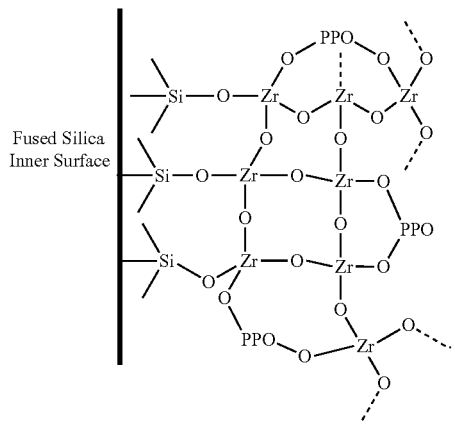

Methods for coating a tube or capillary with a sol-gel are known in the art. In one embodiment, the tube or capillary is filled with a sol solution for a suitable period of time, e.g., from about 10 minutes to about 1 hour, to form a surface bonded sol-gel coating and then any liquid sol is expelled e.g., using gas pressure. The capillary or tube can be thermally conditioned and purged with nitrogen gas. The conditioned capillary can also be washed, e.g., with n-butanol and/or methanol.

The subject invention also concerns methods for preparing a sorbent of the invention. In one embodiment, a modified PPO is prepared so that PPO terminal hydroxyl groups are modified with zirconium tetrachloride. In an exemplified embodiment, the modified PPO comprises the structure:

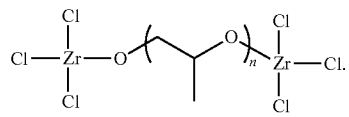

In a specific embodiment of a method for preparing modified PPO, PPO and $ZrCl_4$ are mixed in about a 1:2 molar ratio and dissolved in anhydrous toluene. The solution can be stirred for several hours while being heated.

In one embodiment, a sorbent composition of the invention is prepared via a hydrolytic sol-gel (HSG) method. In one embodiment of the HSG method, a first solution of zirconium butoxide and glacial acetic acid are mixed together. Separately, a second solution of modified PPO and 1-butanol are mixed together, for a suitable period of time (e.g., several hours). The first and second solutions are then mixed together, optionally with water added, for a suitable period of time (e.g., about 6 hours) to produce a sol solution. The prepared sol solution can then be used to coat a capillary or tube surface prior to gelatin of the solution. In a specific embodiment, the method is as shown in Scheme 2.

In another embodiment, a sorbent composition of the invention is prepared via a non-hydrolytic sol-gel (NHSG) method. The sol solution can be prepared using the modified PPO. In one embodiment, $ZrCl_4$ is dissolved in anhydrous butanol to produce a first solution. Separately, as a second solution, modified PPO is mixed in anhydrous toluene for a suitable period of time (e.g., about 6 hours) to allow polymer chains to detach. Subsequently, the butanolic $ZrCl_4$ first solution is mixed with the PPO second solution to produce the sol solution. The prepared sol solution can then be used to coat a capillary or tube surface prior to gelation of the solution. In one embodiment, the NHSG method is as shown in Scheme 3.

The subject invention also concerns methods for extraction and/or enrichment of catecholamines, serotonin, and related compounds (for example, those shown in FIG. 1) in a sample. In one embodiment, the catecholamine is a neurotransmitter, such as dopamine, epinephrine and norepinephrine. In one embodiment, the sample is a biological sample (e.g., urine, saliva, sweat, serum, plasma, blood, lymph, etc.). In a specific embodiment, the sample is an aqueous sample. In one embodiment, the aqueous sample can have a pH that is alkaline (e.g., pH of about 9 to about 11). In one embodiment, the sample is passed through a tube or capillary that has been coated with a sorbent of the present invention. In an exemplified embodiment, the sorbent comprises $ZnO_2PPO$. Following the passing of the sample through the coated tube or capillary, the extracted/enriched product can be desorbed from the coated tube or capillary and then analyzed and/or separated using other chromatographic materials (e.g., GC or HPLC) and methods known in the art.

Sol-gel hybrid $ZrO_2$-PPO sorbents were successfully developed for CME-HPLC analysis. Such sorbents incorporated structural and compositional features that are important for the extraction of polar analytes that require extreme pH conditions. Sol-gel hybrid $ZrO_2$-PPO sorbents offer a pH-stable alternative to conventional silica- or organic polymer-based extraction media. Also, the various intermolecular interactions provided by the presented sorbents avoided the need for derivatization of catecholamines often required for their extraction on polymeric sorbents. The extraction of underivatized catecholamines requires a highly alkaline medium (pH ~10.5) that is detrimental to traditionally used silica-based sorbents. The newly developed sol-gel $ZrO_2$-PPO sorbents can easily withstand such harsh alkaline conditions with excellent stability and reproducibility. The low picomolar limits of detection for dopamine and epinephrine provided by the NHSG $ZrO_2$-PPO sorbents were achieved for the first time compared to the recently published studies. The demonstrated pH stability, excellent sensitivity enhancement factor, analyte desorption efficiency % and the capillary-to-capillary and run-to-run RSD values suggest that the presented sorbents can be advantageously employed in the analysis of catecholamines and their metabolites representing an important biomarkers for neuroendocrine tumors.

Materials and Methods

Materials and Instruments.

Zirconium (IV) butoxide, zirconium (IV) chloride, ethanol, 1-butanol, toluene, 1-dodecanol, hydroxy-terminated polypropylene oxide ($M_{avg}$ 3500), glacial acetic acid, dopamine hydrochloride, epinephrine hydrochloride, and serotonin hydrochloride were purchased from Sigma Aldrich (St. Louis, Mo.). HPLC grade solvents (methanol. dichloromethane, tetrahydrofuran), polypropylene microcentrifuge tubes and micropipette tips were purchased from Fischer Scientific (Waltham, Mass.). Fused silica capillary (250 μm i.d.) with polyimide external protective coating was purchased from Polymicro Technologies (Phoenix, Ariz.). The following chromatographic equipment was used in this study: (a) an Agilent 1100 series HPLC system with a Diode Array Detector (Agilent Inc., Santa Clara, Calif.), (b) a Varian 3800 model gas chromatograph with a flame ionization detector (currently Varian is a part of Agilent), (c) Rhyeodyne 6-ports valve (IDEX Health and Sciences, Oak Harbor, Wash.). (d) an in-laboratory built purging/filling system [31].

Hydrothermal Pretreatment of Fused Silica Capillary.

A one-meter segment of fused silica capillary (250 μm i.d.) was rinsed with 2 mL each of dichloromethane, methanol, and water using a gas pressure-operated purging/filling system [31,32] at 10 psi. Both ends of the capillary were then sealed using an oxy-acetylene torch. The sealed capillary was placed in the GC oven and conditioned by raising the temperature from 40° C. to 350° C. at a rate of 1° C./min, holding the capillary at 350° C. for 200 min. After thermal conditioning, the capillary was cooled to room temperature and cut open on both ends using an alumina wafer. It was then placed in the GC oven with one end connected to the GC injection port, and the other end was left open in the GC oven. Thermal conditioning of the capillary was performed under nitrogen purge (1 mL/min) as follows: (40° C. to 350° C. at rate of 10° C./min, 120 min hold time at 350° C.). The capillary was cooled down to room temperature and its inner surface was ready for coating.

Preparation of Sol-Gel Zirconia-PPO Coated Capillary Via Non-Hydrolytic (NHSG) Route Solvents Drying.

In the non-hydrolytic sol-gel reaction (NHSG) of zirconium tetrachloride, the solvents must be free from water. For this, the solvents (butanol, toluene) were dried over molecular sieve (type 4A) by placing 15 mL of each solvent in a separate vial. A 10-gram amounts of the molecular sieve was added to each solvent and vortexed for 2 minutes and then left airtight in the hood overnight. Two-mL aliquots of each solvent were transferred to a microcentrifuge vial and centrifugation was performed to eliminate any possible contamination from the molecular sieve particles (10,000 rpm for 2 min). To test if the dried solvents still contained water, 0.5 g of anhydrous copper sulfate (white) was mixed with 1 mL of each dried solvent, then the mixture was thoroughly vortexed. The mixture was centrifuged to precipitate the copper sulfate powder, which would turn blue in the presence of water. The drying procedure was repeated until no color change of $CuSO_4$ was observed.

Modification of Organic Polymer with Zirconium Tetrachloride.

Prior to the preparation of the sol-gel sorbents, the terminal hydroxyl groups of polypropylene oxide (PPO) were modified with zirconium tetrachloride. For this, PPO and $ZrCl_4$ were taken in a 25 mL round-bottom flask in molar ratio of 1:2 (PPO: 0.6 mmol, $ZrCl_4$: 1.2 mmol) and dissolved in anhydrous toluene (300 μL). The solution was stirred for 12 hours at 60° C. The solution was then allowed to reach room temperature before using it for the preparation of the sol solution.

Preparation of Sol Solution for the NHSG Route.

The sol solution was prepared as follows: in a polypropylene centrifuge vial, 46 mg of zirconium tetrachloride was dissolved in 74 μL of dry 1-butanol. In a second vial, 80 mg of modified PPO was mixed with 180 of dry toluene and vortexed thoroughly for 1 minute and it was left in the hood for 6 hours allowing the polymer chains to detach. Thereafter, polymer solution was vortexed for 1 minute and then it was transferred to the first vial containing butanolic solution of zirconium tetrachloride. The mixture was vortexed thoroughly to ensure homogeneity. The gelation time of this mixture was ~2 hours. Therefore, the coating of the capillary was performed after allowing the solution to undergo reactions in the vial for only 30 minutes.

Creation of CME Coating Via NHSG Route for CME-HPLC.

Details of sol-gel coating technology can be found elsewhere [31]. Briefly, a 60-cm piece of hydrothermally treated fused silica capillary was installed on a pressure-operated filling/purging system for coating. Under 15 psi nitrogen pressure, the exit end of the capillary was sealed with a rubber septum once the first drop of the sol solution came out of the capillary. Thereafter, the sol solution was allowed to reside in the capillary for 30 min. At the end of the in-capillary residence period, the liquid content of the capillary was expelled under 15 psi gas pressure, leaving behind a sol-gel coating on the capillary inner surface. Nine capillaries were prepared with different in-capillary residence times (starting from 10 minutes in-capillary residence and increasing the time by increments of 5 minutes) to optimize the best coating conditions. The coated capillary was thermally conditioned in a GC oven while simultaneously being purged with a flow of nitrogen gas. For this, one end of the capillary was connected to the GC injection port, and the other end was secured in the GC oven. The capillary was heated using a temperature program (40° C.-150° C. at 1° C./min, with a hold of 300 minutes at 150° C.). The conditioned capillary was cooled down to room temperature and rinsed with 2 mL each of n-butanol and methanol with the help of the purging/filling system. Finally, the coated capillary was thermally conditioned in a GC oven under nitrogen purge (40° C.-150° C. at 5° C./min, with hold time of 300 minutes at 150° C.). At this point, the coated capillary was ready for CME experiments coupled to HPLC.

Preparation of Sol-Gel Zirconia-PPO Coated Capillary Via Hydrolytic Sol-Gel (HSG) Route Preparation of Sol Solution for HSG Route.

The sol-solution was prepared as follows: in a polypropylene centrifuge vial, 70 μL of zirconium butoxide was mixed with 17 μL of glacial acetic acid. In a different vial, 80 mg of modified PPO was mixed with 200 of 1-butanol and vortexed thoroughly for 1 minute and left in the hood for 6 hrs. The polymer solution was then vortexed thoroughly again for 1 minute and then transferred to the first vial containing zirconium butoxide and glacial acetic acid in solution. The mixture was vortexed thoroughly for 2 minutes, and 8 μL of de-ionized water was added to the mixture and followed by thorough vortexing for 2 minutes to ensure homogeneity of the sol-gel solution. The gelation time of this mixture was about 8 hours. Taking this fact in consideration, the sol solution was first allowed to undergo reactions in the vial for 6 hours before using it for coating CME capillary.

Creation of CME Coating Via HSG Route for CME-HPLC

The coating and conditioning procedures for the preparation of sol-gel CME via HSG route were analogous to the one described in the previous section for NHSG route.

Capillary Microextraction Coupled to High Performance Liquid Chromatography (CME-HPLC).

The CME-HPLC experimental setup was described elsewhere [18]. Briefly, a 40-cm piece of the sol-gel coated CME capillary was installed on the HPLC 6-port injection valve as an external sampling loop. In the "sampling" position of the injection port valve, the aqueous sample was allowed to pass through the CME capillary from an in-laboratory designed gravity-fed sample dispenser [32] via the sampling valve. As the sample passed through the capillary, the analytes were extracted by the sol-gel coating on the capillary wall. After 40 min of extraction, the CME-HPLC analysis was started by switching the valve to "inject" position, thereby desorbing the extracted analytes by the HPLC mobile phase flowing through the capillary and transferring them to the HPLC column. The analytes were separated in the HPLC column followed by UV detection.

Characterization of the Synthesized Sol-Gel Materials

Characterization.

FTIR and thermogrametric analysis were performed for HSG and NHSG $ZrO_2$-PPO sorbents. For this, freshly prepared sol solutions (as descried in previous sections) were mixed with hydrothermally pretreated 5 μm diameter silica particles (0.2 g, 5 w/w % of the sol solution weight) in microcentrifuge vial and vortexed for 2 minutes. The prepared mixtures were used to coat the inner surface of borosilicate tube (3.6×6 mm) following a very similar coating/conditioning method as described in previous sections used for the preparation of the sol-gel CME capillaries. The sol-gel materials were scraped off the tube surface with a stainless spatula and were used for FTIR and TGA analysis.

Coating Thickness and Volume.

For the determination of the sol-gel CME coating volume, 10 cross-sectional SEM images (using Hitachi Scanning Electron Microscope SU-70) were taken from 10 random segments (~1-cm) of the prepared sol-gel CME capillaries and the coating average thickness was used to assess the coating volume. The following equation was used for the coating volume: $V=\pi \times h \times (R^2-r^2)$, where, h is the capillary length, R is the fused silica capillary radius from the center to the capillary wall and r is the coated capillary radius from the center to the coating surface (the internal volume of the NHSG CME capillary ~19.17 µL and that for HSG CME capillary ~19.07 µL).

Conversion of Peak Area to Concentration of Extracted Analyte.

The chromatographic peak area was used as a quantitative measure of the extracted analytes. Calibration plots for all analytes were constructed by obtaining the average peak area for 3 replicate measurements conducted by directly injecting each of the standard solutions representing a series of concentrations (0.1-, 0.5-, 1.0-, 5.0-, 25.0-, 50.0-, 75.0-, and 100.0 mg/L). The obtained average peak areas were plotted against the corresponding molar concentration of the injected solutions and best-fit linear equation was used to convert peak area to molar concentration of analytes extracted by the CME capillary.

Analyte Desorption Efficiency (ADE) %.

To evaluate the completeness of desorption of the extracted analytes from the sol-gel CME sorbent coating, each sample was directly injected into the HPLC system using a 40-cm deactivated fused silica capillary as external sampling loop. The obtained peak areas were converted into analyte amounts using the calibration plots as described in the previous section. Each sample (50 mL, containing ~200 ng of analyte) was allowed to pass through the coated capillary for 40 minutes and the liquid exiting from the capillary was collected. The mass of every analyte in the collected liquid was then determined by direct injection into the HPLC system. The difference in the mass of analyte before and after the extraction (evaluated by direct injection) was considered as the extracted amount. After desorbing/analyzing the CME extracted analytes, the obtained mass from this experiment is taken as the desorbed mass. ADE % can then be estimated using the following equation:

$$\text{Analyte Desorption Efficiency \%} = \frac{\text{Desorbed amount}}{\text{Extracted amount}} \times 100$$

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

Sol-gel coating technology was introduced by our group for the creation of chemically stable surface-bonded coatings for capillary electrophoresis [31], open tubular columns gas chromatography (GC) [33], fiber-based solid phase microextraction (SPME) [34], and capillary microextraction (CME) [32]. Sol-gel coating technology provided the stationary phases and extraction media with enhanced level of chemical and thermal stabilities. The key to the success of the sol-gel coating (in addition to the unique physical and chemical properties of the created hybrid materials) is the chemical bonding of the sol-gel coating to the substrate (e.g., fused silica fiber or capillary). The sol-gel reaction route provides a simple, convenient and effective approach to synthesizing organic-inorganic hybrid materials [35]. The resulting hybrid material shows properties that can be useful in different application areas: chromatographic separations [36], sample preparation [37-40], enzymology [41], and diverse range of other applications [42-44].

Metal/metalloid alkoxides are predominantly used as sol-gel precursors for the fabrication of sol-gel materials, due to their high purity, controllable reactivity, and convenience of use. In the hydrolytic route of sol-gel reactions, alkoxide precursors undergo hydrolysis with practically concurrent polycondensation of the hydrolyzed or partially hydrolyzed precursor species among themselves and/or with other sol-gel active species in the solution. The physico-chemical characteristics of the metal/metalloid atom (size, coordination state and partial positive charge δ M), alkoxy group size, together with temperature, solvent, catalyst, etc. represent the most important factors that affect the rate of hydrolysis and condensation of the alkoxide precursors. Compared to silicon alkoxides, zirconium alkoxides undergo significantly faster hydrolysis and condensation (by many orders of magnitude) [11,45,46]. In $Zr(OEt)_4$, the partial positive charge on zirconium is +0.65. By comparison, in $Ti(OEt)_4$ the partial charge on Ti is +0.63 and in $Si(OEt)_4$ the partial positive charge is +0.32 on Si. For instance, such differences in partial charges and other parameters for zirconium and silicon result in greatly higher rate of hydrolysis ($k_h \sim 10^{-2}$ $M^{-1}$ $s^{-1}$) for $Zr(OEt)_4$ precursor compared to hydrolysis rate for $Si(OEt)_4$ ($k_h \sim 5 \times 10^{-9}$ $M^{-1}$ $s^{-1}$) [11,46]. In addition to the difference in the rate of hydrolysis, the condensation rate of hydrolyzed zirconium alkoxide precursor is significantly higher than analogous rate for silicon precursors ($k_c \sim 30$ $M^{-1}$ $s^{-1}$ vs. $10^{-4}$ $M^{-1}$ $s^{-1}$) [11,45]. Thus, preferential formation of zirconia is likely to occur when silica-based sol-gel active ligands or polymers are mixed with zirconium alkoxide. In a sol-gel system that contains precursors with vastly different reactivities, there exists a great probability of preferential reaction taking place with the participation of chemical species characterized by higher reactivities. To create hybrid material systems by integrating different sol-gel-active species, it is important that the chemical reactivities of these species are close to each other. To that end, different solvents and chelating agents have been used to slow down the hydrolysis and condensation rates of transition metal alkoxides precursors [16,47-49]. We employed functionalization of hydroxyl-terminated polypropylene oxide with zirconium tetrachloride (see Scheme 1), to provide a silica-free organic polymer having sol-gel-active terminals with reaction rates comparable to that for zirconia-based sol-gel precursors. The modification reaction of PPO was conducted in anhydrous toluene at 60° C. with continuous stirring analogous to a recent study [30] but without microwave-heating of the reaction mixture. Acetic acid was used as a chelating reagent to reduce the fast hydrolysis rate for zirconia precursors for the synthesis of the $ZrO_2$-PPO sorbent via HSG route [16,50]. The zirconium trichloride groups on the terminals of PPO have hydrolysis ($k_h \sim 2.1 \times 10^{-2}$ $M^{-1}$ $s^{-1}$) [51], comparable to that of zirconium alkoxide precursors ($k_h \sim 10^{-2}$ $M^{-1}$ $s^{-1}$) [45]. Condensation reactions (either water-condensation or alcohol condensations) take place between different components of the sol solution leading to the formation of a three-dimensional hybrid organic-inorganic network (Scheme 2).

Scheme 1.
Illustration of the modification of PPO with zirconium tetrachloride

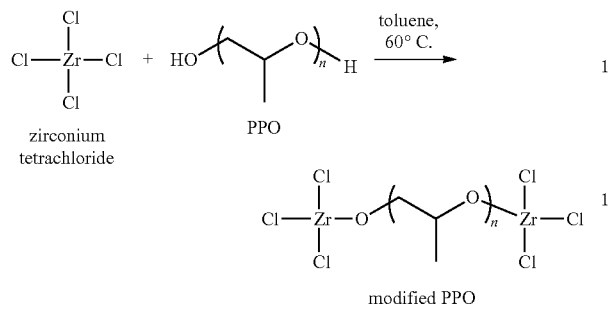

Scheme 2.
Illustration of the HSG route for the preparation of sol-gel ZrO$_2$—PPO sorbent

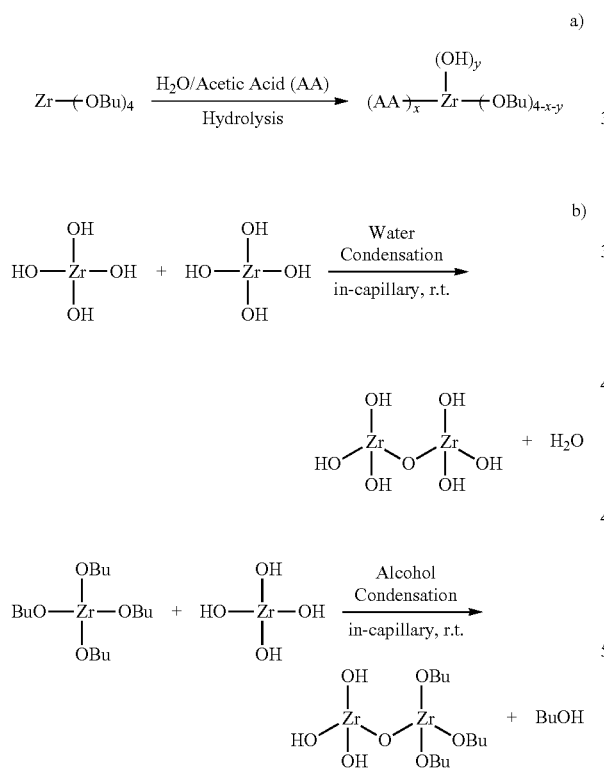

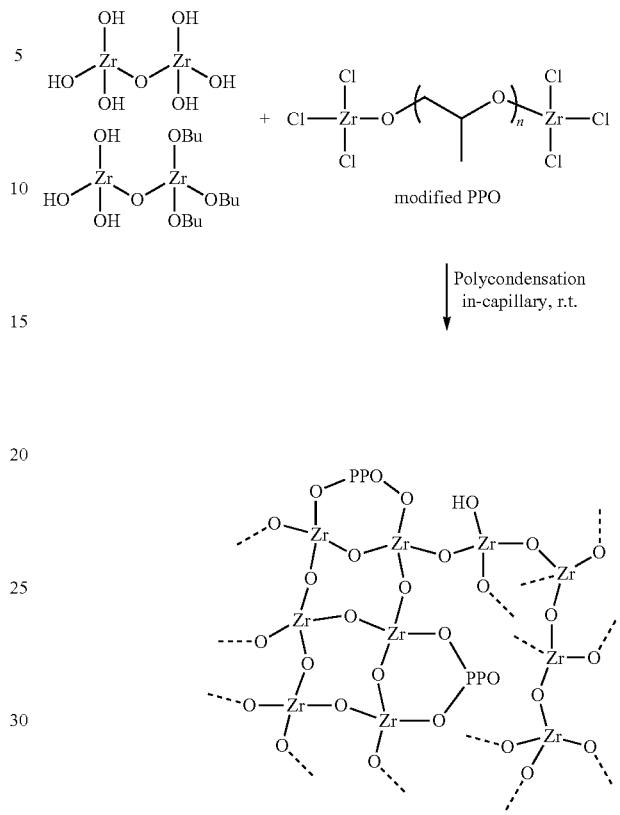

Two types of structural and physiochemical characteristics encouraged us to use PPO as the organic component for the proposed hybrid sorbents: (a) the ability to provide H-bonding interactions and the amphiphilic character provided intermolecular interactions facilitated the extraction of catecholamines, (b) these forces also allowed for the creation of homogeneous sol solution composed of organic and inorganic components.

For the preparation of the NHSG ZrO$_2$-PPO sorbent, zirconium tetrachloride underwent alcoholysis as depicted in Scheme 3-a, and concurrently condensation via butyl chloride elimination (Scheme 3-b). Polycondensation occurred for the sol-gel components in the presence of the modified PPO as shown in Scheme 3-c. The hybrid organic-inorganic zirconia-based sorbent was synthesized in situ by conducting the sol-gel reaction within the capillary where it had the opportunity to undergo condensation reaction with the silanol groups on the inner surface of fused silica capillary as shown in Scheme 3-d.

Scheme 3.
Illustration of the NHSG route for the preparation of sol-gel ZrO$_2$—PPO sorbent,
(a) the alcoholysis of ZrCl$_4$, (b) the condensation followed by (c) polycondensation with modified PPO and (d) the condensation of the prepared sorbent on the inner surface of fused silica capillary.

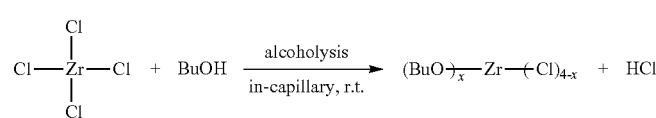

-continued

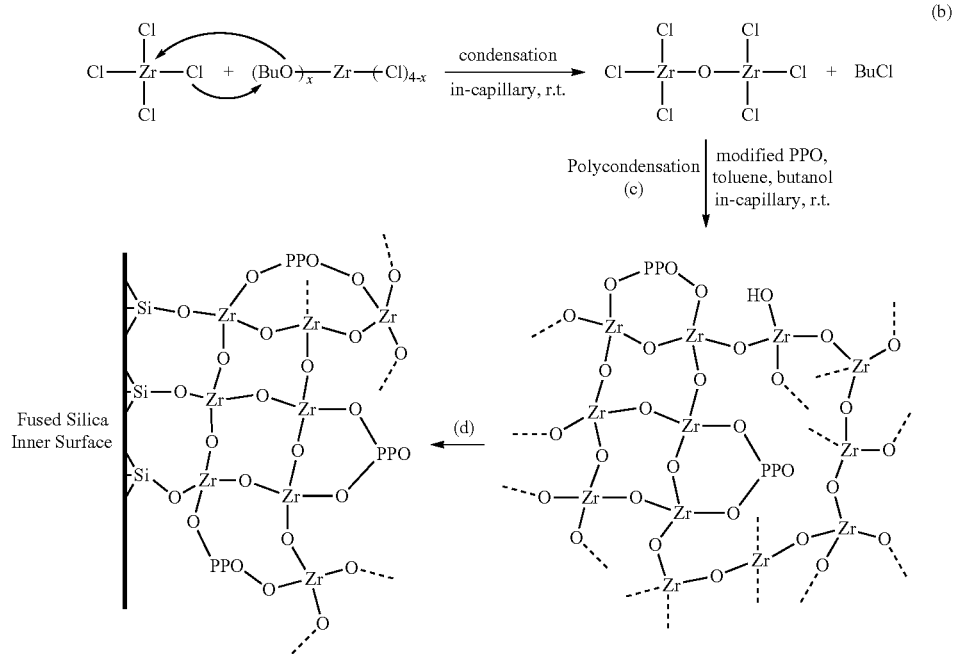

Figures 2A, 2B:
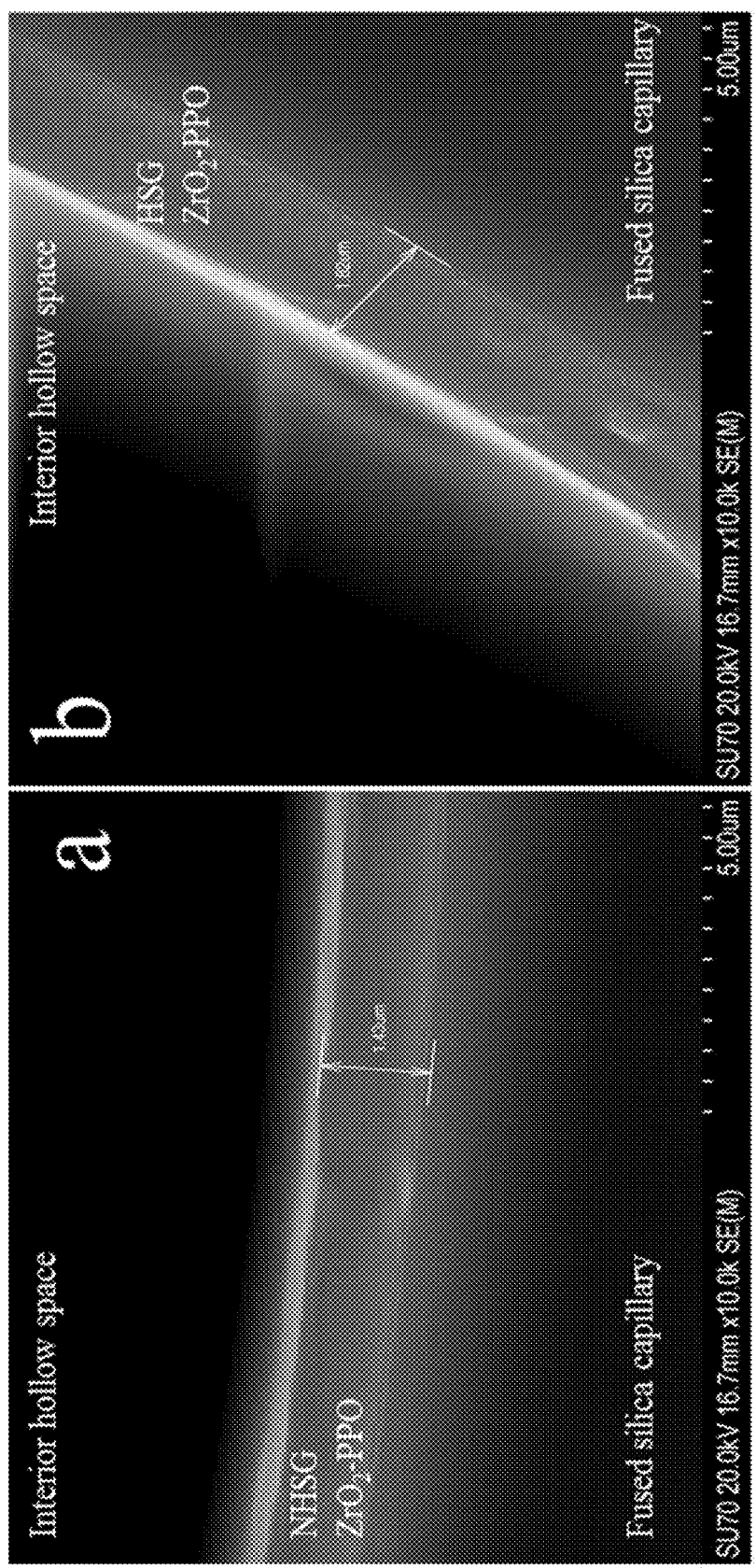
FIGS. 2A-2B. Illustration of scanning electron microscopic images of (FIG. 2A) NHSG $ZrO_2$-PPO coated capillary and (FIG. 2B) HSG $ZrO_2$-PPO coated capillary at 10,000 magnification.

FIGS. 2A-2B illustrate the scanning electron microscopic images of the cross-sectional view for both NHSG and HSG coated capillaries. The average coating thickness calculated from 10 segments of coated capillaries was (1.49 μm and 1.81 μm for NHSG and HSG coatings, respectively) used for the estimation of the coating volume.

Figure 3:
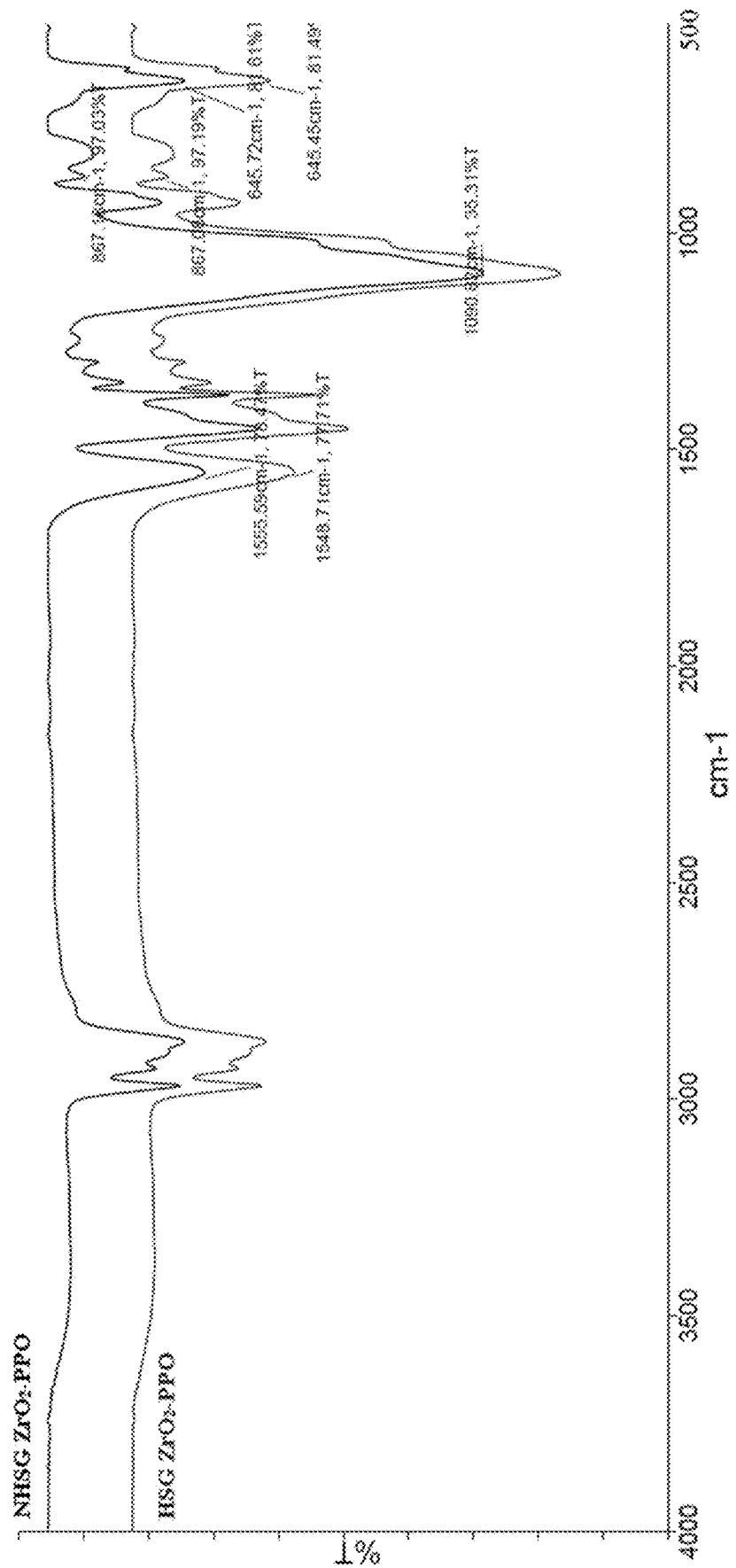
FIG. 3. FTIR spectra for sol-gel sorbent prepared via NHSG (black) and HSG (red) routes.

The results from FTIR spectroscopy investigation are shown in FIG. 3. Here, the peaks at 1555 and 1548 cm$^{-1}$ are indicative of the presence of Zr—O—C bond [52] in the sol-gel material prepared by NHSG (black) and HSG (red) routes, respectively. The obtained sol-gel material mimic the composition and coating conditions used for the preparation of the sol-gel sorbents in the CME capillary. As evident by FTIR spectra, the peak at 867 cm$^{-1}$ can be attributed to the presence of Zr—O—Si bond [53] between the sol-gel material and the silica particles. This data also indicates the feasibility of creating such covalent bonding between the sol-gel zirconia-based sorbents and the fused silica surface of the CME capillary. The sol-gel material prepared via hydrolytic route was treated with water to fully hydrolyze the residual zirconium tetrabutoxide precursors that might have undergone only partial hydrolysis or have not undergone hydrolysis at all during the synthesis. The presence of such species could interfere with the FTIR analysis by showing the presence of Zr—O—C bond between Zr and butoxide groups. This data provides evidence for the successful chemical bonding of PPO to the zirconia sol-gel network and the ability of the presented sol-gel coating routes to create covalently bonded sorbents on fused silica surface.

Figure 4B:
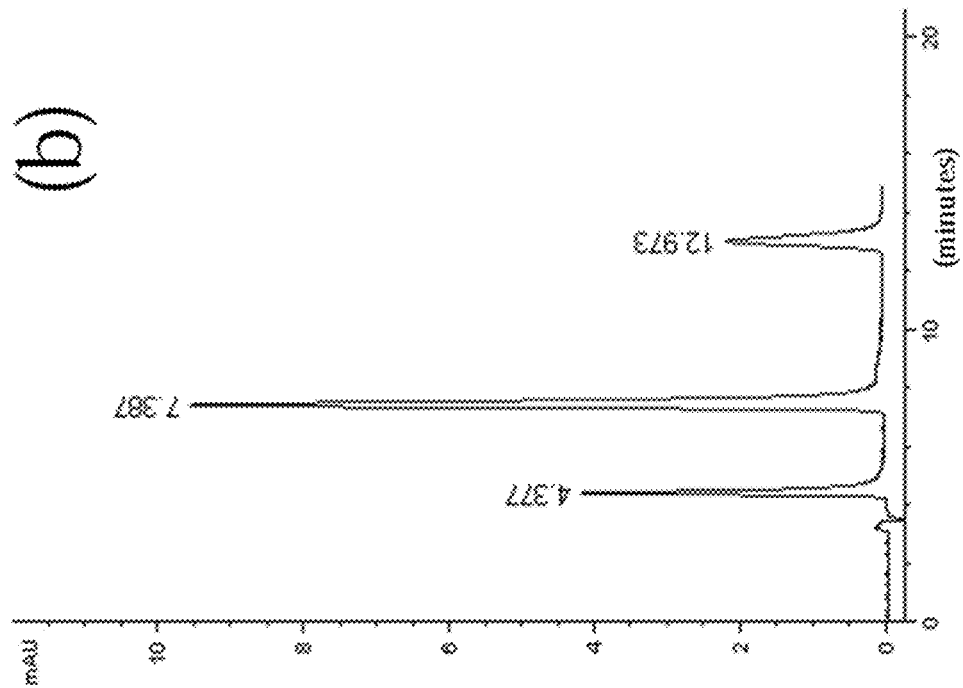
FIGS. 4A-4B. CME-HPLC-UV chromatograms of nicotinic acid, serotonin, and acetaminophen extracted from aqueous sample at room temperature and concentration level at 100 µg/L (FIG. 4A) before and (FIG. 4B) after treating the coated capillary with 1 M NaOH, water, 1 M HCl then water. The extraction was performed using NHSG $ZrO_2$-PPO sorbent. Mobile phase composition: 90:10% ammonium acetate (20 mM, pH 3.8):methanol. Detector conditions: DAD at 225 nm. Alltech $C_{18}$ HPLC column (250×2 mm).
Figure 4A:
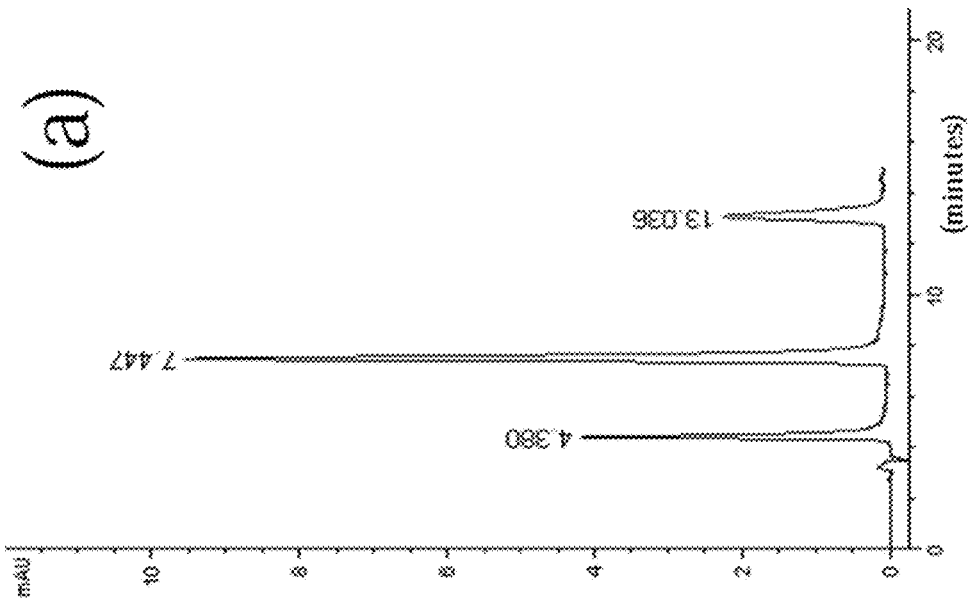

Sol-gel coating method for the creation of hybrid sorbents with excellent chemical- and pH-stability has been investigated. Malik et al. synthesized and evaluated the analytical performance of sol-gel titania-[15,19,20], zirconia-[16], and germania-[14,17,18] based hybrid sorbents which showed excellent pH-stability (0-14). To examine the chemical and pH stabilities of the prepared sol-gel sorbent. CME-HPLC experiments were conducted using a CME capillary coated with NHSG ZrO$_2$-PPO. The capillary was rinsed with 1.0 M HCl aqueous solution for a period of 6 hours followed by rinsing with 50-mL of deionized water. The coated capillary was further rinsed with 1.0 M NaOH aqueous solution for a period of 6 hours and then was washed again with 50-mL of deionized water. FIGS. 4A-4B show the CME-HPLC chromatograms obtained for the comparison of CME performance of the prepared sol-gel zirconia-PPO coated capillary before and after the exposure to harsh pH conditions. It clearly shows the stability of the sol-gel CME coating since its extraction capability remained practically unchanged. A comparison of the peak areas of these two chromatograms revealed a slight peak area increase (0.9%, 0.18%, and 0.37% for nicotinic acid, serotonin and acetaminophen, respectively) obtained by CME-HPLC experiments conducted after rinsing the capillary with extreme-pH solutions. The slight increase in the extraction capability of the sorbent can be attributed to the renewed availability of some buried extraction sites on the surface of the sol-gel sorbent due to removal of possible surface contaminants by harsh pH solutions.

Figure 5:
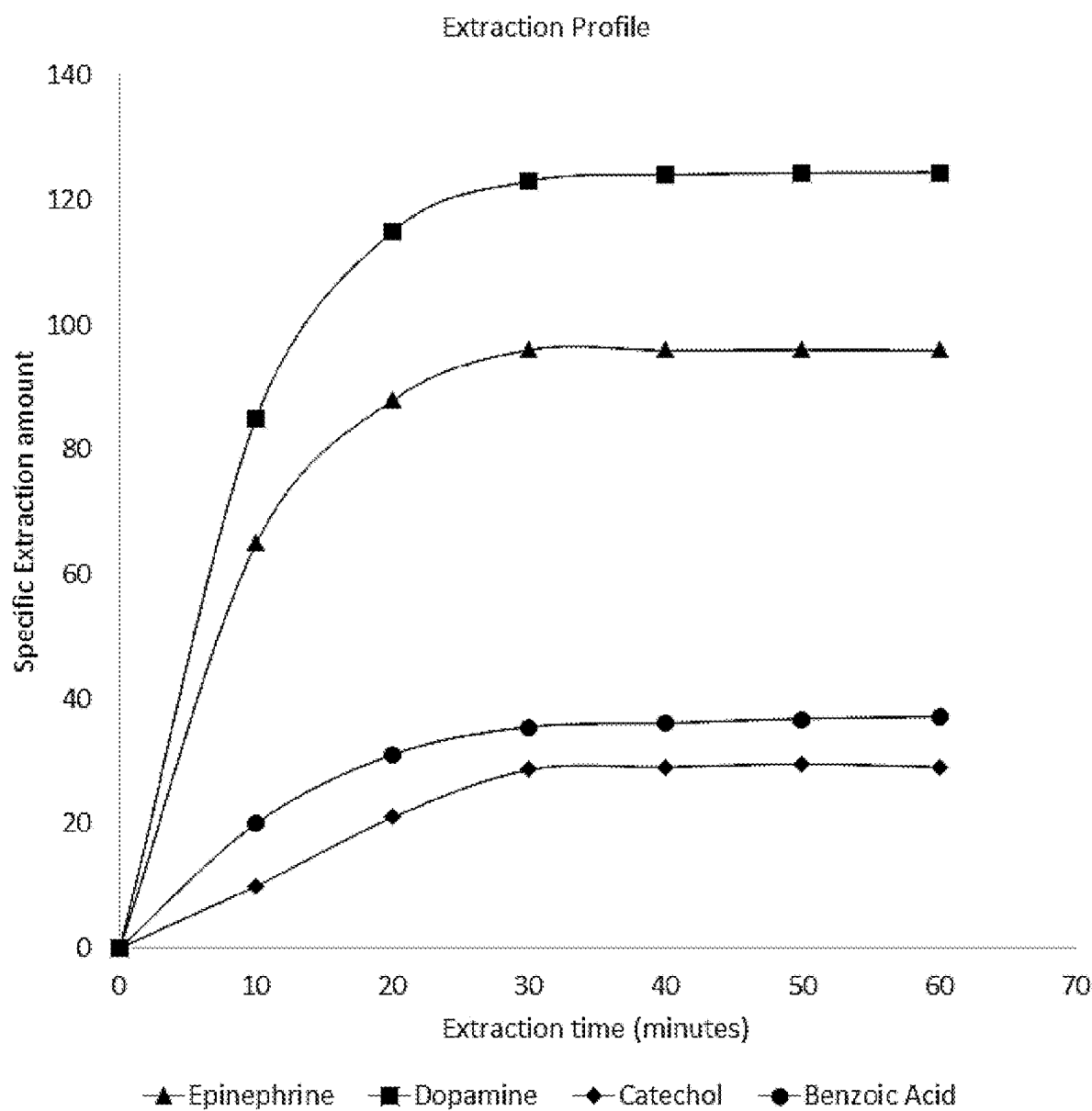
FIG. 5. Extraction profile for dopamine, epinephrine, catechol, benzoic acid using NHSG $ZrO_2$-PPO sorbent. Mobile phase composition: catechol-, resorcinol-, quinol 70:30% ammonium acetate (20 mM, pH 3.8):methanol. For dopamine and epinephrine 98:2% ammonium acetate (20 mM, pH 3.8):methanol. Detector conditions: DAD at 225 nm. Alltech $C_{18}$ HPLC column (250×2 mm).

To determine the time-required to establish the extraction equilibrium of the target analytes between the sol-gel sorbents and the sample matrix, extraction profiles were experimentally constructed. FIG. 5 presents extraction profiles on a NHSG coated capillary. Benzoic acid, catechol, dopamine, and epinephrine were extracted and the time-required to establish analyte equilibrium between the sample matrix and the sol-gel sorbent was estimated as the point on the time axis that corresponded to the start of the plateau on the extraction curve. The HSG coated capillary provided an analogous extraction behavior for the same analytes.

Catecholamines metabolites such as homovanillic acid (HVA), 3-methoxy-4-hydroxyphenylglycol (MHPG) and vanillylmandelic acid (VMA) possess chemical structures (shown in FIG. 1) with similar chemical groups such as hydroxyl- and methoxy-groups, cis-diol, carboxylic acid and benzene ring. Catechol, resorcinol, quinol, vanillin, acetaminophen, benzoic acid and 4-hydroxybenzoic acid were used as test probes containing similar functional groups as on the catecholamine metabolites. FIG. 1 and the chemical structures of the molecules structurally related to the metabolites reveal the resemblance of the used chemical probes to the deaminated metabolites. Table 1 represents results from CME-HPLC-UV experiments using a sol-gel $ZrO_2$-PPO sorbent obtained via NHSG and HSG routes. The obtained results show excellent run-to-run reproducibility (RSD 1.5-3.2%) and picomolar-level limits of detection ranging from 260 to 820 pM obtained by HSG $ZrO_2$-PPO sorbent. Also, HSG sorbent provided higher affinity toward catechol compared to its isomers (resorcinol and quinol) as revealed by the specific extraction amount (SEA) values (about ~90% higher than quinol and 130% higher than resorcinol). SEA values pertains the extracted analyte mass per unit mass of sorbent, which helps to evaluate the selective interactions of the sorbent toward various analytes with different functional groups allowing for effective comparison of the performance of different extraction media with different ligands and formats [54]. The higher affinity toward catechol can be attributed to the interaction between the bidentate sides of the two neighboring hydroxyl (cis-diol groups) on catechol with zirconium atom (Lewis acid). The extracted mass of 4-hydroxybenzoic (pKa 4.52) was higher than the extracted mass of benzoic acid (pKa 4.2) by 13.5%. Since zirconia-based sorbents are oxophilic (interact with oxygen-containing molecules) the observed higher extraction and higher SEA value of 4-hydroxybenzoic acid compared to benzoic acid can be attributed to possible additional Lewis acid-base interaction between the hydroxyl group on 4-hydroxybenzoic acid and the Lewis acid sites on the sorbent surface.

Figure 6:
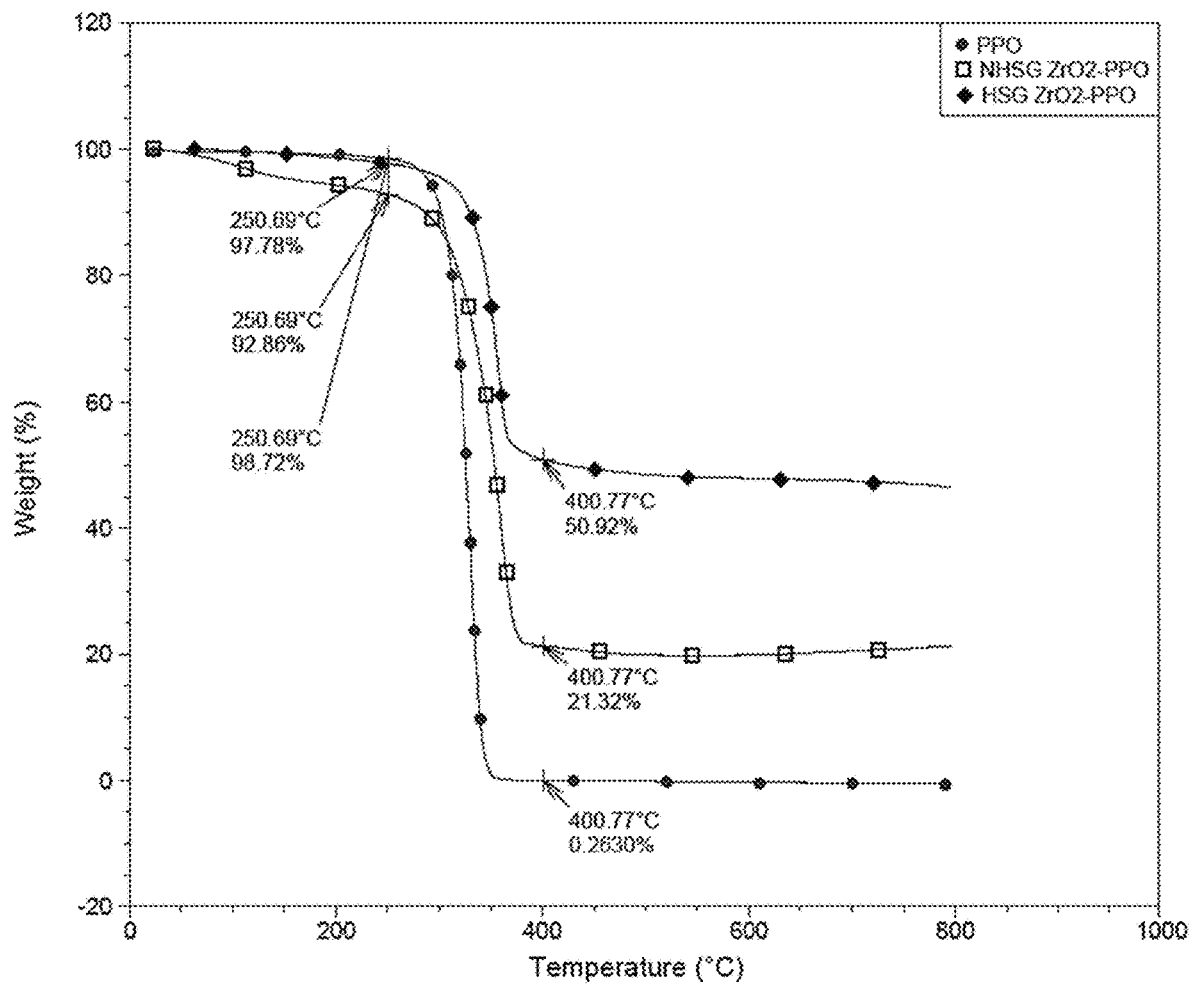
FIG. 6. Illustration of the TGA curves for unreacted-PPO, NHSG $ZrO_2$-PPO and HSG $ZrO_2$-PPO.

NHSG sorbent facilitated significantly better extraction performance and enhancement factor compared to HSG sorbent. Although the run-to-run peak area reproducibility was slightly better for the HSG sorbents as shown in Table 1, the achieved LODs by NHSG sorbent are lower by about 1~2 order of magnitude. Excellent LODs provided by NHSG sorbents for these deaminated probes ranges between 7.9-38.1 pmol/L. The lower limits of detection achieved using NHSG sorbent can be explained by the followings: a) nonhydrolytic route of sol-gel reactions is known to produce more Lewis-acid sites than Bronsted-base sites on the surface of the sol-gel materials [23] (b) non hydrolytic sol-gel route has successfully incorporated higher amount of the organic polymer into the sol-gel network. Lewis acid-base intermolecular interactions (150-400 kJ/mol) [55], are stronger than the intermolecular forces associated with hydroxyl groups (H-bonding 5-60 kJ/mol or charge assisted H-bonding 60-120 kJ/mole) [56]. To investigate the difference in the loading of PPO in these two sorbents, thermogravimetric analysis was performed on HSG and NHSG sorbents scraped off the surface of glass tube as well as on a sample of PPO not incorporated in sol-gel material. As is evident from the TGA data (FIG. 6), the NHSG sorbent contains significantly higher percent of PPO than the HSG sorbent. Furthermore, it was noticed that the pyrolysis temperature of PPO somewhat increased in the case of hybrid organic-inorganic sol-gel sorbents compared with free PPO. This can be attributed to the collective effect of covalent bonding and intercalation of PPO to/within the sol-gel network.

TABLE 1

CME-HPLC-UV results of various analytes in aqueous sample at 100 μg/L concentration level, extracted using HSG and NHSG zirconia-PPO sorbents. HPLC conditions: catechol, resorcinol, quinol (mobile phase composition 70:30% ammonium acetate (20 mM):methanol, DAD at 225 nm). For vanillin, 4-hydroxybenzoic acid, and acetaminophen (90:10% ammonium acetate (20 mM):methanol, DAD at 280 nm). Alltech $C_{18}$ HPLC column (250 × 2 mm). Number of trials n = 3, signal-to-noise ratio (S/N = 3).

| | Run-to-run RSD (%) | | LOD (pM) | | SEA (μg/g) | |
|---|---|---|---|---|---|---|
| | NHSG | HSG | NHSG | HSG | NHSG | HSG |
| Catechol | 5.6 | 1.5 | 36.3 | 320 | 24.53 | 21.24 |
| Resorcinol | 6.1 | 3.2 | 36.3 | 700 | 9.683 | 9.72 |
| Quinol | 1.8 | 2.1 | 38.1 | 600 | 13.49 | 11.16 |
| Acetaminophen | 7.2 | 3.1 | 19.2 | 270 | 18.06 | 14.35 |
| 4-hydroxybenzoic acid | 2.9 | 2.7 | 7.9 | 446 | 36.88 | 20.53 |
| Benzoic Acid | 3.1 | 1.4 | 9.1 | 820 | 28.9 | 18.08 |
| Vanillin | 3.1 | 2.1 | 10.6 | 260 | 25.48 | 19.69 |

Figure 7:
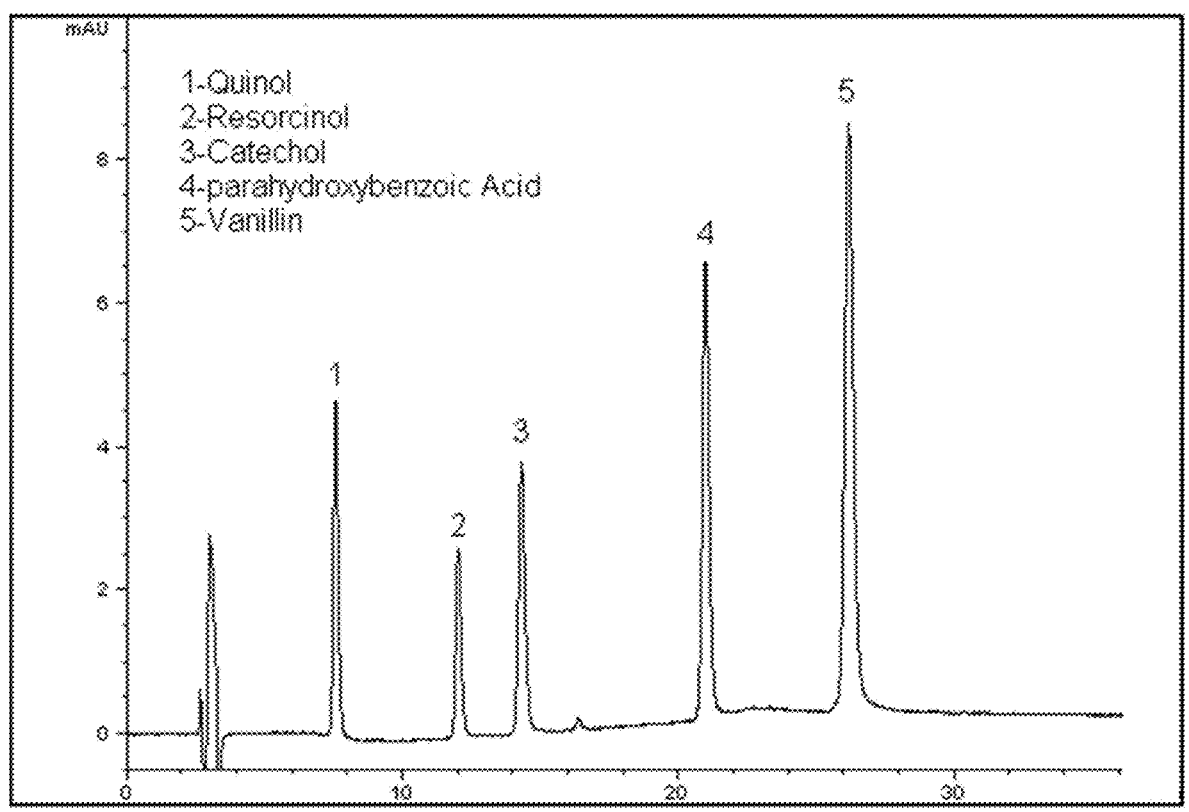
FIG. 7. CME-HPLC-UV chromatogram of quinol, resorcinol, parahydroxybenzoic acid, acetaminophen (at 100 µg/L concentration level) and catechol (at 50 µg/L concentration level) extracted from aqueous sample, using NHSG zirconia-PPO sorbent. Mobile phase composition: minute 0, 90:10% ammonium acetate (20 mM, pH 3.8):methanol, minute 20:70:30% ammonium acetate (20 mM, pH 3.8): methanol. DAD at 225 nm. Alltech $C_{18}$ HPLC column (250×2 mm).
Figure 8:
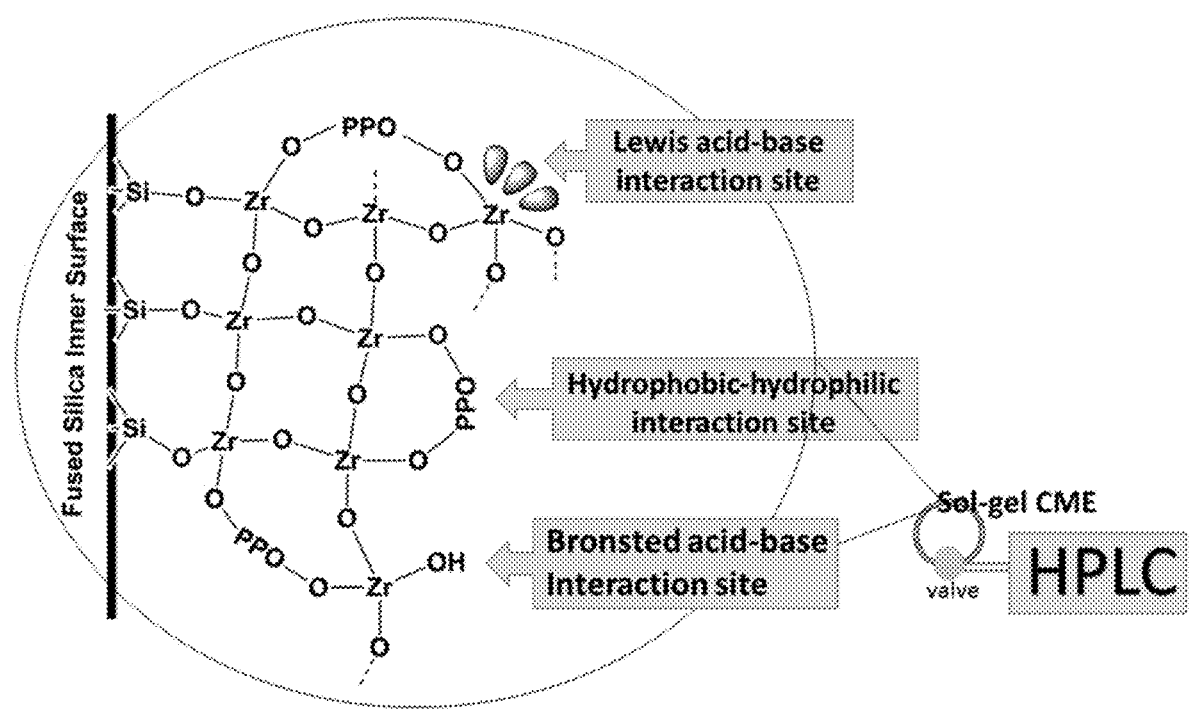
FIG. 8. Graphical Abstract.

FIG. 7 represent chromatograms obtained for CME-HPLC analysis of quinol, resorcinol, catechol, acetaminophen and 4-hydroxybenzoic acid extracted from an aqueous sample. Excellent performance of the sorbent in simultaneous extraction of multiple target analytes is evident from this chromatogram. This is important in the analysis of catecholamines and their metabolites, since quantifying the ratio of these biomarkers is key to the estimation of the state of the cancer in the adrenal gland [57].

Dopamine, epinephrine, and serotonin were selected due to their important role in the human body as neurotransmitters and biomarkers for neuroendocrine cancer types. A good number of the recently published studies lack LC-MS compatibility because of the need for using ion pairing reagents or non-volatile additives in the mobile phase. Other studies are based on chemical derivatization of catecholamines prior to analysis which may cause lengthy analysis procedures and loss of sample during derivatization. This study utilizes an LC-MS compatible mobile phase (ammonium acetate buffer, 20 mM) and it is derivatization-free which shows the applicability of the sol-gel $ZrO_2$-PPO coatings in capillary microextraction for the clinical investigations of the catecholamines and their metabolites. To maximize the extraction efficiency of the sol-gel sorbents for catecholamines, the pH of the aqueous samples containing dopamine and epinephrine were adjusted using aqueous ammonia solution to pH 10.5 (~two pH units higher than the isoelectric point (pI) of catecholamines which ranges between 8.5 to 9.0) [58]. Due to stability issues, the use of such a high pH level is problematic with silica-based sorbents.

Table 2 represents CME-HPLC-UV results for dopamine, epinephrine and serotonin using HSG and NHSG zirconia-PPO sorbents. Excellent analyte desorption efficiency (ADE) % was obtained for dopamine, epinephrine and serotonin using NHSG and HSG sorbents (~95-99.5%). The NHSG $ZrO_2$-PPO sorbent provided significantly lower LODs when compared to HSG $ZrO_2$-PPO sorbents. NHSG $ZrO_2$-PPO achieved LOD of 5.6 pmol/L and 9.59 pmol/L for epinephrine and dopamine, respectively. While those for HSG $ZrO_2$-PPO sorbents were 270 pmol/L and 350 pmol/L for dopamine and epinephrine, respectively. Also, the sensitivity enhancement factor [59] by the NHSG $ZrO_2$-PPO sorbent was higher than that of the HSG sorbent by 6.0, 27.4 and 4.0 folds for epinephrine, dopamine and serotonin, respectively. The achieved LODs using the NHSG $ZrO_2$-PPO sorbents surpasses the LODs for dopamine and epinephrine in many reported studies (54 pM-27 nM) [8,60-78], which can be attributed to both the Lewis acid sites on the surface of zirconia sorbents [50,79,80] and the ability of the non-hydrolytic sol-gel route to incorporate high content of the PPO into the resulting sorbents.

TABLE 2

CME-HPLC-UV results for epinephrine, dopamine and serotonin extracted from aqueous sample (pH 10.5) at 100 μg/L concentration level, extracted using HSG and NHSG zirconia-PPO sorbents. Mobile phase composition: 98:2% ammonium acetate (20 mM, pH 3.8):methanol. DAD at 225 nm. Alltech $C_{18}$ HPLC column (250 × 2 mm). Number of trials n = 3, signal-to-noise ratio (S/N = 3).

| | Run-to-run RSD % (n = 3) | | LOD (pM) | | Mass Extracted (ng) | | ADE % | | SEA (μg/g) | | Sensitivity Enhancement Factor | |
|---|---|---|---|---|---|---|---|---|---|---|---|---|
| | NHSG | HSG | NHSG | HSG | NHSG | HSG | NHSG | HSG | NHSG | HSG | NHSG | HSG |
| Epinephrine | 3.6 | 2.5 | 5.6 | 340 | 72.72 | 6.13 | 94.9 | 99.5 | 96.96 | 3.84 | 1297 | 218 |
| Dopamine | 5.1 | 0.6 | 9.59 | 270 | 93.3 | 15.99 | 96.5 | 98.5 | 124.4 | 9.99 | 2332 | 85 |
| Serotonin | 4.7 | 0.8 | 9.6 | 290 | 38.98 | 11.95 | 98.6 | 98.8 | 50.6 | 7.47 | 653 | 163 |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES (1) Pacak, K.; Eisenhofer, G.; Ahlman, H.; Bornstein, S. R.; Gimenez-Roqueplo, A. P.; Grossman, A. B.; Kimura, N.; Mannelli, M.; McNicol, A. M.; Tischler, A. S.; International Symposium on, P. *Nat. Clin. Pract. Endocrinol. Metab.* 2007, 3, 92-102.
(2) Manger, W. M.; Gifford, R. W. *J. Clin. Hybertens.* 2002, 4, 62-72.
(3) Oasis Sample Extraction Products Brochure. WATERS Literature Notes. Publication Number 720001692EN.
(4) Pastoris, A.; Cerutti, L.; Sacco, R.; De Vecchi, L.; Sbafi, A. *J. Chromatogr. B* 1995, 664, 287-293.
(5) Sabbioni, C.; Saracino, M. A.; Mandrioli, R.; Pinzauti, S.; Furlanetto, S.; Gerra, G.; Raggi, M. A. *J. Chromatogr. A* 2004, 1032, 65-71.
(6) Vuorensola, K.; Sirén, H. *J. Chromatogr. A* 2000, 895, 317-327.
(7) Unger, K. K.; Liapis, A. I. *J. Sep. Sci.* 2012, 35, 1201-1212.
(8) Rozet, E.; Morello, R.; Lecomte, F.; Martin, G. B.; Chiap, P.; Crommen, J.; Boos, K. S.; Hubert, P. *J. Chromatogr. B* 2006, 844, 251-260.
(9) Piest, M.; Zhang, X.; Trinidad, J.; Engbersen, J. F. J. *Soft Matter* 2011, 7, 11111-11118.
(10) Phenylboronic Acid (PBA) Solid Phase Extraction Mechanisms and Applications. *Agilent Technologies Technical Overview*. Publication Number SI-02442. 2010.
(11) C. Brinker, G. S. *Sol-Gel Science: The Physics and Chemistry of Sol-Gel Processing; Academic Press,* 1990.
(12) McCalley, D. V. *J. Chromatogr. A* 1993, 636, 213-220.
(13) Nawrocki, J.; Dunlap, C.; McCormick, A.; Carr, P. W. *Journal of Chromatography A* 2004, 1028, 1-30.
(14) Segro, S. S.; Triplett, J.; Malik, A. *Anal. Chem.* 2010, 82, 4107-4113.
(15) Kim, T.-Y.; Alhooshani, K.; Kabir, A.; Fries, D. P.; Malik, A. *J. Chromatogr. A* 2004, 1047, 165-174.
(16) Alhooshani, K.; Kim, T.-Y.; Kabir, A.; Malik, A. *J. Chromatogr. A* 2005, 1062, 1-14.
(17) Fang, L.; Kulkarni, S.; Alhooshani, K.; Malik, A. *Anal. Chem.* 2007, 79, 9441-9451.
(18) Segro, S. S.; Malik, A. *J. Chromatogr. A* 2010, 1217, 5746-5752.
(19) Malik, A.; Kim, T.-Y. U.S. Pat. No. 7,622,191, 2009.
(20) Segro, S. S.; Cabezas, Y.; Malik, A. *J. Chromatogr. A* 2009, 1216, 4329-4338.
(21) Debecker, D. P.; Mutin, P. H. *Chem. Soc. Rev.* 2012, 41, 3624-3650.
(22) Debecker, D. P.; Hulea, V.; Mutin, P. H. *Appl. Catal., A* 2013, 451, 192-206.
(23) Mutin, P. H.; Vioux, A. *Chem. Mater.* 2009, 21, 582-596.
(24) Pinna, N.; Niederberger, M. *Angewandte Chemie* 2008, 47, 5292-5304.
(25) Mutin, P. H.; Vioux, A. *Chem. Mater.* 2009, 21, 582-596.
(26) Bilecka, I.; Niederberger, M. *Electrochimica Acta* 2010, 55, 7717-7725.
(27) Nagarajan, S.; Mohana, M.; Sudhagar, P.; Raman, V.; Nishimura, T.; Kim, S.; Kang, Y. S.; Rajendran, N. *ACS applied materials & interfaces* 2012, 4, 5134-5141.
(28) Nagarajan, S.; Mohana, M.; Sudhagar, P.; Raman, V.; Nishimura, T.; Kim, S.; Kang, Y. S.; Rajendran, N. *ACS applied materials & interfaces* 2012, 4, 5134-5141.
(29) Sudha, M.; Senthilkumar, S.; Hariharan, R.; Suganthi, A.; Rajarajan, M. *J. Sol-Gel Sci. Technol.* 2012, 65, 301-310.
(30) Morselli, D.; Niederberger, M.; Bilecka, I.; Bondioli, F. *J Nanopart Res* 2014, 16, 2645-2655.
(31) Hayes, J. D.; Malik, A. *J. Chromatogr. B* 1997, 695, 3-13.
(32) Bigham, S.; Medlar, J.; Kabir, A.; Shende, C.; Alli, A.; Malik, A. *Anal. Chem.* 2002, 74, 752-761.
(33) D. Wang, S. C., A. Malik. *Anal. Chem.* 1997, 69, 4566-4576.
(34) Chong, S.; Wang, D.; Hayes, J.; Wilhite, B.; Malik, A. *Anal. Chem.* 1997, 69, 3889-3898.
(35) Kelly, J. A.; Henderson, E. J.; Veinot, J. G. *Chem. Commun.* 2010, 46, 8704-8718.
(36) Hayes, J. D.; Malik, A. *Anal. Chem.* 2000, 72, 4090-4099.
(37) Segro, S. S.; Tran, M. P.; Kesani, S.; Alhendal, A.; Turner, E. B.; Abdul, M. *J. Sep. Sci.* 2010, 33, 3075-3096.

(38) Bagheri, H.; Piri-Moghadam, H.; Naderi, M. *TrAC Trends in Anal. Chem.* 2012, 34, 126-139.
(39) Kabir, A.; Furton, K. G.; Malik, A. *TrAC Trends in Analytical Chemistry* 2013, 45, 197-218.
(40) Fumes, B. H.; Silva, M. R.; Andrade, F. N.; Nazario, C. E. D.; Lancas, F. M. *TrAC Trends in Analytical Chemistry* 2015, 71, 9-25.
(41) Chen, Z.; Hayashi, K.; Iwasaki, Y.; Kurita, R.; Niwa, O.; Sunaawa, K. *Electroanalysis* 2005, 17, 231-238.
(42) Li, X.; Shen, J. *Thin Solid Films* 2011, 519, 6236-6240.
(43) Jeevajothi, K.; Subasri, R.; Soma Raju, K. R. C. *Ceram. Int.* 2013, 39, 2111-2116.
(44) Minami, T. *J. Sol-Gel Sci. Technol.* 2013, 65, 4-11.
(45) Livage, J.; Henry, M.; Sanchez, C. *Prog. Solid State Chem.* 1988, 18, 259-341.
(46) Wright, J. D.; Sommerdijk, N. *Sol-gel Materials Chemistry and Applications*; Gordon and Breach Science Publishers, Amsterdam, 2001, p 53-57.
(47) Fujita, K. *Bull. Chem. Soc. Jpn.* 2012, 85, 415-432.
(48) Suh, D. J.; Park, T.-J.; Han, H.-Y.; Lim, J.-C. *Chem. Mater.* 2002, 14, 1452-1454.
(49) Yoldas, B. E. *J. Mater. Sci.,* 21, 1087-1092.
(50) Randon, J.; Huguet, S.; Piram, A.; Puy, G.; Demesmay, C.; Rocca, J. L. *J. Chromatogr. A* 2006, 1109, 19-25.
(51) Fang, Z.; Dixon, D. A. *J. Phys. Chem. C* 2013, 117, 7459-7474.
(52) Aronne, A.; Sannino, F.; Bonavolonta, S. R.; Fanelli, E.; Mingione, A.; Pernice, P.; Spaccini, R.; Pirozzi, D. *Environ. Sci. Technol.* 2012, 46, 1755-1763.
(53) Chang, C.-C.; Hwang, F.-H.; Hsieh, C.-Y.; Chen, C.-C.; Cheng, L.-P. *J. Coat. Technol. Res.* 2013, 10, 73-78.
(54) Seyyal, E.; Malik, A. *J. Chromatogr. A* in press.
(55) Skinner, H. A.; Conner, J. A. *Pure Appl. Chem.* 1985, 57, 79-88.
(56) Steed, J. W.; Atwood, J. L. *Supramolecular Chemistry*, 2nd ed.; Wiley: UK, 2009.
(57) Strenger, V.; Kerbl, R.; Dornbusch, H. J.; Landenstein, R.; Ambros, P. F.; Ambros, I. M.; Urata, C. *Pediatr. Blood Cancer* 2007, 48, 504-509.
(58) Kartsova, L. A.; Sidorova, A. A.; Kazakov, V. A.; Bessonova, E. A.; Yashin, A. Y. *J. Anal. Chem.* 2004, 59, 826-831.
(59) Bu, Y.; Feng, J.; Sun, M.; Zhou, C.; Luo, C. *Anal. Bioanal. Chem.* 2016, 1-12.
(60) Talwar, D.; Williamson, C.; McLaughlin, A.; Gill, A.; O'Reilly, D. S. *J. Chromatogr. B* 2002, 769, 341-349.
(61) Baranyi, M.; Milusheva, E.; Vizi, E. S.; Sperlagh, B. *J. Chromatogr. A* 2006, 1120, 13-20.
(62) Thomas, A.; Geyer, H.; Mester, H. J.; Schänzer, W.; Zimmermann, E.; Thevis, M. *Chromatographia* 2006, 64, 587-591.
(63) Vlčková, M.; Schwarz, M. A. *J. Chromatogr. A* 2007, 1142, 214-221.
(64) Wang, S.-C.; Shih, H.-H.; Rossi, D. T.; Campbell, W. *Microchem. J.* 2007, 87, 163-169.
(65) Ji, C.; Li, W.; Ren, X.-d.; El-Kattan, A. F.; Kozak, R.; Fountain, S.; Lepsy, C. *Anal. Chem.* 2008, 80, 9195-9203.
(66) Lasakova, M.; Thiebaut, D.; Jandera, P.; Pichon, V. *J. Sep. Sci.* 2009, 32, 1036-1042.
(67) Whiting, M. J. *Ann. Clin. Biochem.* 2009, 46, 129-136.
(68) Zhang, X.; Xu, S.; Lim, J. M.; Lee, Y. I. *Talanta* 2012, 99, 270-276.
(69) Dunand, M.; Gubian, D.; Stauffer, M.; Abid, K.; Grouzmann, E. *Anal. Chem.* 2013, 85, 3539-3544.
(70) Lin, T. H.; Lu, C. Y.; Tseng, W. L. *Electrophoresis* 2013, 34, 297-303.
(71) Claude, B.; Morin, P.; Denoroy, L. *J. Liq. Chromatogr. Relat. Technol.* 2014, 37, 2624-2638.
(72) Ferry, B.; Gifu, E.-P.; Sandu, I.; Denoroy, L.; Parrot, S. *J. Chromatogr. B* 2014, 951-952, 52-57.
(73) Ankireddy, S. R.; Kim, J. Int. *J. Nanomed* 2015, 10, 113-119.
(74) Chen, L.-Q.; Wang, Y.; Qu, J.-S.; Deng, J.-J.; Kang, X.-*J. Biomed. Chromatogr.* 2015, 29, 103-109.
(75) Chitravathi, S.; Munichandraiah, N. *J. Electrochem. Soc.* 2015, 162, B163-B172.
(76) Ferrer, D. G.; Garcia, A. G.; Peris-Vicente, J.; Gimeno-Adelantado, J. V.; Esteve-Romero, *J. Anal. Bioanal. Chem.* 2015, 407, 9009-9018.
(77) Ma, H.-F.; Chen, T.-T.; Luo, Y.; Kong, F.-Y.; Fan, D.-H.; Fang, H.-L.; Wang, W. *Microchim. Acta* 2015, 182, 2001-2007.
(78) Saracino, M. A.; Santarcangelo, L.; Raggi, M. A.; Mercolini, L. *J. Pharm. Biomed. Anal.* 2015, 104, 122-129.
(79) de Bellaistre, M. C.; Mathieu, O.; Randon, J.; Rocca, J. L. *J. Chromatogr. A* 2002, 971, 199-205.
(80) Gaweł, B.; Gaweł, K.; Øye, G. *Mater.* 2010, 3, 2815-2833.

We claim:

1. A metal or metalloid oxide-based sol-gel hybrid sorbent composition prepared from a biocompatible polymer or ligand comprising one or more sol-gel active end groups, wherein the sorbent composition comprises the structure:

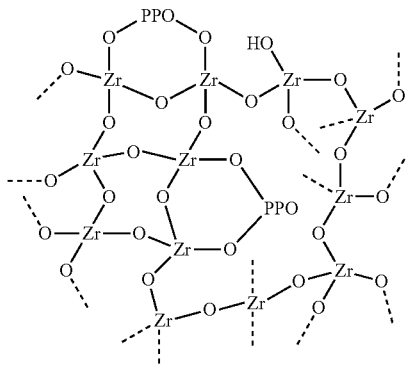

wherein PPO has the structure:

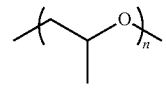

wherein n is an integer ≥1.

2. The sorbent composition according to claim 1, wherein the polymer or ligand used to prepare the sorbent composition comprises one or more sol-gel active end groups selected from hydroxyl group, alkoxy group, derivatized hydroxyl group, derivatized alkoxy group, or any combination thereof.

3. The sorbent composition according to claim 1, wherein the polymer or ligand is chemically anchored in the sol-gel via chemical bonding of one end of the polymer or ligand, or bonding of both or all ends of the polymer or ligand, or any combination thereof.

4. A hollow tube or capillary coated on the inner surface with a metal or metalloid oxide-based sol-gel hybrid sorbent composition, wherein the sorbent composition attached to the inner surface comprises the structure:

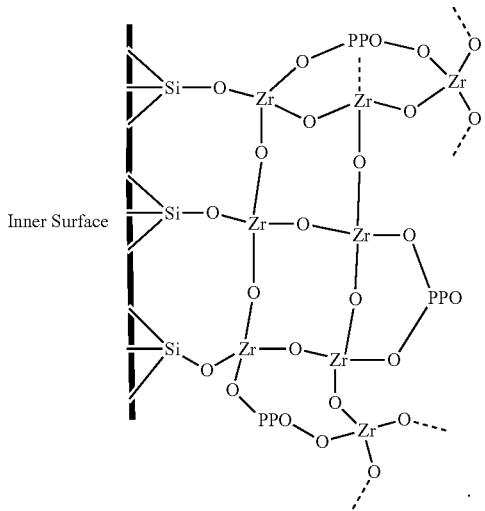

5. The tube or capillary according to claim 4, wherein the tube or capillary is composed of fused silica or comprises an inner surface of fused silica.

6. The tube or capillary according to claim 5, wherein the fused silica is hydrothermally treated fused silica.

7. A method for preparing a metal or metalloid oxide-based sol-gel hybrid sorbent, wherein the method comprises synthesis by a hydrolytic sol-gel (HSG) method as shown in Scheme 2 or synthesis by a non-hydrolytic sol-gel (NHSG) method as shown in Scheme 3.

8. The method according to claim 7, wherein the method comprises
   i) mixing a solution of zirconium butoxide and acetic acid;
   ii) mixing a solution of modified polypropylene oxide (PPO) and butanol;
   iii) combining the solutions of step (i) and step (ii) to produce a solution of a sol-gel hybrid sorbent.

9. The method according to claim 8, further comprising coating the interior wall of a hollow tube or capillary with the solution of the sol-gel hybrid sorbent of step (iii) for a sufficient period of time to provide for bonding of the sol-gel hybrid sorbent to the wall of the tube or capillary, and optionally thermally conditioning the sorbent coated tube or capillary.

10. The method according to claim 7, wherein the method comprises
    i) dissolving $ZnCl_4$ in butanol to produce a first solution;
    ii) mixing a modified PPO in toluene to produce a second solution;
    iii) combining the solutions of step (i) and step (ii) to produce a solution of a sol-gel hybrid sorbent.

11. The method according to claim 10, further comprising coating the interior wall of a hollow tube or capillary with the solution of the sol-gel hybrid sorbent of step (iii) for a sufficient period of time to provide for bonding of the sol-gel hybrid sorbent to the wall of the tube or capillary, and optionally thermally conditioning the sorbent coated tube or capillary.

12. A method for extraction and/or enrichment of one or more catecholamines, or catecholamine metabolites, or a related compound in a sample, the method comprising passing the sample through a hollow tube or capillary coated on the inner surface with a metal or metalloid oxide-based sol-gel hybrid sorbent composition, and then desorbing the extracted analyte from the sorbent of the tube or capillary wall, wherein the sorbent composition comprises the structure:

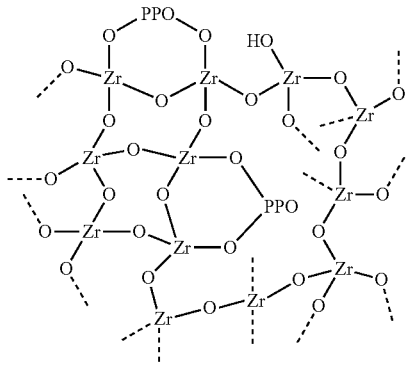

wherein PPO has the structure:

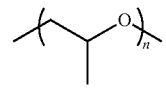

wherein n is an integer $\geq 1$.

13. The method according to claim 12, wherein the sample is a biological sample.

14. The method according to claim 12, wherein the sample is an aqueous sample and optionally has an alkaline pH.

* * * * *

UNITED STATES PATENT AND TRADEMARK OFFICE
CERTIFICATE OF CORRECTION

PATENT NO.         : 10,618,030 B2
APPLICATION NO.    : 15/639449
DATED              : April 14, 2020
INVENTOR(S)        : Abdul Malik and Abdullah Awadh Alhendal Page 1 of 1

It is certified that error appears in the above-identified patent and that said Letters Patent is hereby corrected as shown below:

In the Specification

Column 5,

Line 15, " 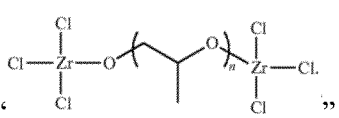 " should read -- 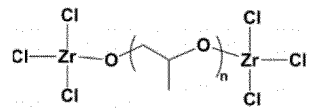 --

Column 7,
Line 36, "180 of dry" should read --180 µL of dry--

Column 8,
Line 15, "with 200 of" should read --with 200 µL of--

Signed and Sealed this
Eighteenth Day of August, 2020

Andrei Iancu
*Director of the United States Patent and Trademark Office*